(12) United States Patent
Takahashi et al.

(10) Patent No.: US 8,173,387 B2
(45) Date of Patent: May 8, 2012

(54) METHOD OF EXAMINING CHEMICAL USING GENE-DISRUPTED STRAIN

(75) Inventors: Junko Takahashi, Tsukuba (JP); Chiaki Kato, Tsukuba (JP)

(73) Assignee: Daikin Industires, Ltd., Osaka (JP)

( * ) Notice: Subject to any disclaimer, the term of this patent is extended or adjusted under 35 U.S.C. 154(b) by 730 days.

(21) Appl. No.: 10/581,085

(22) PCT Filed: Nov. 30, 2004

(86) PCT No.: PCT/JP2004/017779
§ 371 (c)(1),
(2), (4) Date: Aug. 12, 2008

(87) PCT Pub. No.: WO2005/054511
PCT Pub. Date: Jun. 16, 2005

(65) Prior Publication Data
US 2009/0246755 A1    Oct. 1, 2009

(30) Foreign Application Priority Data
Dec. 2, 2003    (JP) ................................. 2003-403350

(51) Int. Cl.
*C12Q 1/02* (2006.01)
*C12Q 1/68* (2006.01)
(52) U.S. Cl. .......................................... 435/29; 435/6.1
(58) Field of Classification Search ........................ None
See application file for complete search history.

(56) References Cited

U.S. PATENT DOCUMENTS

| | | | |
|---|---|---|---|
| 5,948,612 A * | 9/1999 | Bascomb et al. ................ | 435/6 |
| 2001/0031724 A1* | 10/2001 | Roemer et al. .................... | 514/2 |
| 2002/0103154 A1 | 8/2002 | Dimster-Denk | |
| 2003/0180953 A1 | 9/2003 | Roemer et al. | |
| 2004/0248126 A1 | 12/2004 | Iwahashi et al. | |
| 2005/0112573 A1 | 5/2005 | Iwahashi et al. | |

FOREIGN PATENT DOCUMENTS

| | | |
|---|---|---|
| JP | 2001-095596 A | 4/2001 |
| JP | 2001-238694 A | 9/2001 |
| JP | 2001-286281 A | 10/2001 |
| WO | WO-03/010333 A2 | 2/2003 |
| WO | WO-03/010333 A3 | 2/2003 |
| WO | WO-03-018791 A1 | 3/2003 |
| WO | WO-03-018792 A1 | 3/2003 |

OTHER PUBLICATIONS

Monarca et al, Mutation Research, Genet. Toxicol. and Environ. Mutagenesis 490: 159 (2001).*
Kitagawa et al.; "Effects of the Pensticide Thiuram: Genome-wide Screening of Indicator Genes by Yeast DNA Microarray"; Environmental Science and Technology; vol. 36, No. 18; pp. 3908-3915; Sep. 15, 2002.
Ramos et al.; "Molecular Analysis of the *Saccharomyces cerevisiae* YHR076w Gene"; IUBMB LIFE; vol. 50, No. 6, pp. 371-377; XP008102277 England; Dec. 2000.
Nicolas Page et al.; "A *Saccharomyces cerevisiae* Genome-Wide Mutant Screen for Altered Sensitivity to K1 Killer Toxin"; Genetics; Mar. 2003; vol. 163 No. 3 pp. 875-894.
Guri Giaever et al.; "Genomic Profiling of drug sensitivities via induced haploinsufficiency"; Nature Genetics; Mar. 1999; vol. 21 No. 3 pp. 278-283.
Biswas Subhrajit et al.; "N-Acetylglucosamine-inducible CAGAP1 encodes a general amino acid permease which co-ordinates external nitrogen source response and morphogenesis in *Candida albicans*"; Microbiology; Sep. 2003; vol. 149 No. 9 pp. 2597-2608.
K.L. Jensen-Pergakes et al.; "Sequencing, Disruption, and Characterization of the *Candida albicans* Sterol Methyltransferase (ERG6) Gene: Drug Susceptibility Studies in erg6 Mutants"; Antimicrobial Agents and Chemotherapy; May 1998; vol. 42 No. 5 pp. 1160-1167.
Kelly et al.; "Genome-wide generation of yeast gene deletion strains"; Comparative and Functional Genomics; Aug. 2001; vol. 2 No. 4 pp. 236-242.
Eloi Gari et al.; "A Set of Vectors with a Tetracycline-Regulatable Promoter System for Modulated Gene Expression in *Saccharomyces cerevisiae*" Yeast; 1997; vol. 13 No. 9 pp. 837-848.
Marianne D. De Backer et al.; Genomic Profiling of the Response of *Candida albicans* to Itraconazole Treatment Using a DNA Microarray; Antimicrobial Agents and Chemotherapy; Jun. 2001; vol. 45 No. 6 pp. 1660-1670.
Marianne D. De Backer et al.; "Recent Developments in Molecular Genetics of *Candida albicans*"; Annual Review of Microbiography; 2000; vol. 54 pp. 463-498.

* cited by examiner

*Primary Examiner* — James Martinell
(74) *Attorney, Agent, or Firm* — Global Conselors

(57) ABSTRACT

A method having higher sensitivity in a bioassay method utilizing cell response of a microorganism, for detecting the presence of a chemical in a test specimen is provided. The method of the present invention is characterized in that it uses specified gene-disrupted strains.

19 Claims, 6 Drawing Sheets

METHOD OF EXAMINING CHEMICAL USING GENE-DISRUPTED STRAIN

CROSS-REFERENCE TO RELATED APPLICATIONS

This U.S. National stage application claims priority under 35 U.S.C. §119(a) to Japanese Patent Application No. 2003-403350, filed in Japan on Dec. 2, 2003, the entire contents of which are hereby incorporated herein by reference.

TECHNICAL FIELD

The present invention relates to a method of examining a chemical present in a specimen in the environment.

BACKGROUND ART

A human being has previously produced a huge number of chemical substances, and new chemicals are developed every year. These chemicals are utilized in every aspect of a modern life, and serve in improving a life of a human being. To the contrary, among chemicals, some are released into the environment at a variety of stages such as manufacturing, distribution, use, disposal and the like, and adversely influence on health of a human and an ecosystem through remaining in the environment, and biological concentration due to a food chain, and environmental pollution has become a social problem. Therefore, there is demand for assessing influence of a chemical on a human body and an ecosystem.

When a chemical present in a test specimen to be detected, it is very important to improve a detection sensitivity of a detection system. When only a chemical having a low concentration is present in a test specimen, a test specimen must be concentrated depending on a detection sensitivity of a detection system which is used for detecting a chemical having a low concentration. However, in order to concentrate an aqueous solution such as an environmental specimen, a concentrating apparatus becomes necessary. In addition, when a subject chemical is volatile, a chemical is lost by a concentration procedure in some cases. For this reason, a detection system requiring necessity of concentrating procedure as little as possible, that is, an assay system having a high detection sensitivity is desired.

For detecting a chemical present in the environment, there is an assay system utilizing toxicity response of a yeast cell See, for example, WO 03/018792 and Japanese Patent Publication No. 2003-061676).

SUMMARY OF THE INVENTION

Problems to be Solved by the Invention

The present inventors accumulated gene information induced by chemicals as shown in WO 03/018792 and Japanese Patent Publication No. 2003-061676, and have been studied a bioassay method utilizing toxicity response of a yeast cell. A sensitivity for detecting a chemical by bioassay depends on sensitivity of a cell and an organism using as an index on a chemical. Therefore, in a bioassay method utilizing toxicity response of a yeast cell, it is necessary to utilize a yeast cell having a higher sensitivity in order to construct a system of a higher sensitivity. Then, from about 4800 kinds of gene-disrupted strains which can be grown as a homozygous diploid among gene-disrupted strains of 6000 kinds of genes of yeast, gene-disrupted strains having a chemical sensitivity suitable in an assay system for detecting a chemical were selected.

An object of the present invention is to provide a method having a higher sensitivity in a bioassay method utilizing toxicity response of a microorganism.

Means to Solve the Problems

That is, the present invention relates to:
A first aspect of the present invention is a method of examining whether a chemical is present in a test specimen or not, comprising culturing a gene-disrupted stain of a microorganism in the presence of the test specimen, and using cell response of the gene-disrupted strain to the chemical as an index, preferably the method in which cell response of the gene-disrupted strain to the chemical is life or death of a cell, and/or a change in the proliferating ability, an aspiration amount, enzyme activity and/or gene expression, further preferably
the method in which the change in gene expression is a change in a RNA amount or a mRNA amount, more preferably
the method in which the change in gene expression is measured by reporter·gene·assay, A second aspect of the present invention is the method according to the first aspect, wherein the microorganism is yeast, preferably
the method in which a gene to be disrupted, according to classification of public database: MITS, is classified into
amino acid metabolism (01.01), nitrogen and sulfur metabolism (01.02), nucleotide metabolism (01.03), phosphate metabolism (01.04), C-compound and carbohydrate metabolism (01.05), lipid, fatty acid and isoprenoid metabolism (01.06), metabolism of vitamins, cofactors and prosthetic groups (01.07) of metabolism (01);
  DNA processing (03.01), cell cycle (03.03) of cell cycle and DNA processing (03);
  mRNA transcription (04.05), RNA transport (04.07) of transcription (04);
  ribosome biosynthesis (05.01), translational control (05.07) of protein synthesis (05); protein targeting, sorting, translocation (06.04), protein modification (06.07), assembly of protein complex (06.10), proteolysis (06.13) of protein fate (06);
nuclear transport (08.01), vesicular transport (Golgi network etc.) (08.07), vacuolar transport (08.13), cellular import (08.19), cytoskeleton-dependent transport (08.22), other intracellular transport activities (08.99) of intracellular transport and transport mechanism (08); stress response (11.01), toxicification (11.07) of cell rescue, defense and pathogenicity (11); ionic homeostasis (13.01), cell sensitivity and response (13.11) of intracellular environmental regulation/interaction (13);
cell growth/morphogenesis (14.01), cell differentiation (14.04) of cell fate (14); cell wall (30.01), cytoskeleton (30.04), nucleus (30.10), mitochondria (30.16) of cell tissue control (30);
ion transporter (67.04), vitamin/cofactor transporter (67.21), transport mechanism (67.50), other transport promotion (67.99) of transport promotion (67);
  unclassified (98); and/or
  unclassified protein (99), further preferably
the method in which the gene to be disrupted is involved in the function of the following Table 2, more preferably, the method in which the gene to be disrupted is involved in a vacuole, for example, in the case of yeast, specifically, the following YPR036W, YDR027C, YHR026W, YHR039C-A, YKL080W, YLR447C, YGR105W, YKL119C, YHR060W (wherein YHR039C-A is designated as YHR039C-B in some cases), more specifically, the method in which the gene to be disrupted is (2-1) YGL026C, YGR180C, YDR127W, YCR028C, YLR284C, YOR221C, YAL021C, YGL224C, YBL042C, YDR148C, YHL025W, YLR307W, YLR345W, YLR354C, YPL129W or YPR060C which is a metabolism (01) gene;

(2-2) YGR180C, YDR150W, YGL240W, YBL058W, YIL036W, YLR226W, YLR381W, YOR026W, YPL018W, YBL063W, YDR363W-A, YIR026C, YLR234W, YMR032W or YPL129W which is a cell cycle and DNA processing (03) gene;

(2-3) YGR006W, YIL036W, YKR082W, YLR226W, YML112W, YMR021C, YAL021C, YDR195W, YOL068C, YBR279W, YGL070C, YGL071W, YGL222C, YHL025W, YLR266C or YPL129W which is a transcription (04) gene;

(2-4) YBL058W, YLR287C-A, YGR084C or YLR344W which is a protein synthesis (05) gene;

(2-5) YKL080W, YLR447C, YGL240W, YGR105W, YGL206C, YKL119C, YDR414C, YHR060W, YLR292C, YLR306W, YGL227W or YGR270W which is a protein fete (06) gene;

(2-6) YPR036W, YDR027C, YHR039C, YKL080W, YLR447C, YGL206C, YKR082W, YLR292C or YBL063W which is an intracellular transport and transport mechanism (08) gene;

(2-7) YJR104C or YMR021C which is a detoxification (11) gene;

(2-8) YPR036W, YHR039C, YKL080W, YLR447C, YGL071W or YIR026C which is an intracellular regulation/interaction (13) gene;

(2-9) YDL151C, YBL058W, YKR082W, YDL151C, YOL068C, YDR363W-A, YHL025W, YIR026C, YLR307W, YMR032W or YPL129W which is a cell fate (14) gene;

(2-10) YDR027C, YDR414C, YLR381W, YGR084C or YMR032W which is cell tissue control (30) gene;

(2-11) YPR036W, YHR026W, YHR039C, YKL080W, YLR447C, YCR028C or YLR292C which is a transport promotion (67) gene;

(2-12) YBL056W which is an unclassified (98) gene; or (2-13) YDR149C, YLR285W, YLR311C, YOR331C, YPR123C, YDR525W-A, YDR539W, YDR540C, YGL246C, YJL204C, YLR282C, YLR287C, YLR290C, YJL188C, YJL192C, YJL211C, YKL037W, YLR283W, YLR312C, YLR315W, YLR320W or YPL030W which is an unclassified (99) gene;

A third aspect of the present invention is the method according to the first aspect, wherein the microorganism is a microorganism other than yeast, and the gene to be disrupted is a gene corresponding to a gene as defined in the (2), A fourth aspect of the present invention is a kit comprising a gene-disrupted strain of a microorganism, which is used for examining whether a chemical is present in a test specimen or not, preferably, the kit, wherein cell response to a chemical is life or death of a cell, and/or a change in the proliferating ability, aspiration amount, enzyme activity and/or gene expression, further preferably, the kit, wherein the change in gene expression is a change in a RNA amount or a mRNA amount, more preferably, the kit, wherein the change in gene expression is measured by reporter·gene·assay, A fifth aspect of the present invention is the kit according to the fourth aspect, wherein the microorganism is yeast and the gene to be disrupted is defined in the (2), and the kit according to the (4), wherein the microorganism is a microorganism other than yeast, and the gene to be disrupted is a gene corresponding to a gene as defined in the (2), A sixth aspect of the present invention is a composition for examining whether a chemical is present in a test specimen or not, comprising a gene-disrupted strain of a microorganism, preferably, the composition, wherein cell response to a chemical is life or death of a cell, and/or a change in the proliferating ability, an aspiration amount, enzyme activity and/or gene expression, further preferably, the composition, wherein the change in gene expression is a change in a RNA amount or a mRNA amount, more preferably, the composition, wherein the change in gene expression is measured by reporter·gene·assay, A seventh aspect of the present invention is the composition according to the the sixth aspect, wherein the microorganism is a microorganism other than yeast, and the gene to be disrupted is defined in the second aspect, and the composition according to the sixth aspect, wherein the microorganism is a microorganism other than yeast, and the gene to be disrupted is a gene corresponding to a gene as defined in the second aspect, and An eighth aspect of the present invention is a use of a gene-disrupted strain of a microorganism for examining whether a chemical is present in a test specimen or not, preferably, the use, wherein cell response to a chemical is life or death of cell a and/or a change in the proliferating ability, an aspiration amount, enzyme activity and/or gene expression, further preferably, the use, wherein the change in gene expression is a change in a RNA amount or a mRNA amount, more preferably, the use, wherein the change in gene expression is measured by reporter·gene·assay, A ninth aspect of the present invention is the use according to the eighth aspect, wherein the microorganism is a microorganism other than yeast, and the gene to be disrupted is defined in the second aspect, and the use according to the eighth aspect, wherein the microorganism is a microorganism other than yeast, and the gene to be disrupted is a gene corresponding to a gene as defined in the second aspect.

Effect of the Invention

The present invention is a highly sensitive assay system which can suitably detect a chemical even when only a chemical having a low concentration is present in a test specimen. Since the assay system of the present invention has a high sensitivity, it is not necessary to concentrate a test specimen and, since concentration is not necessary, even when a subject chemical is volatile, a chemical can be suitably detected.

DETAILED DESCRIPTION OF THE INVENTION

Figure 1:
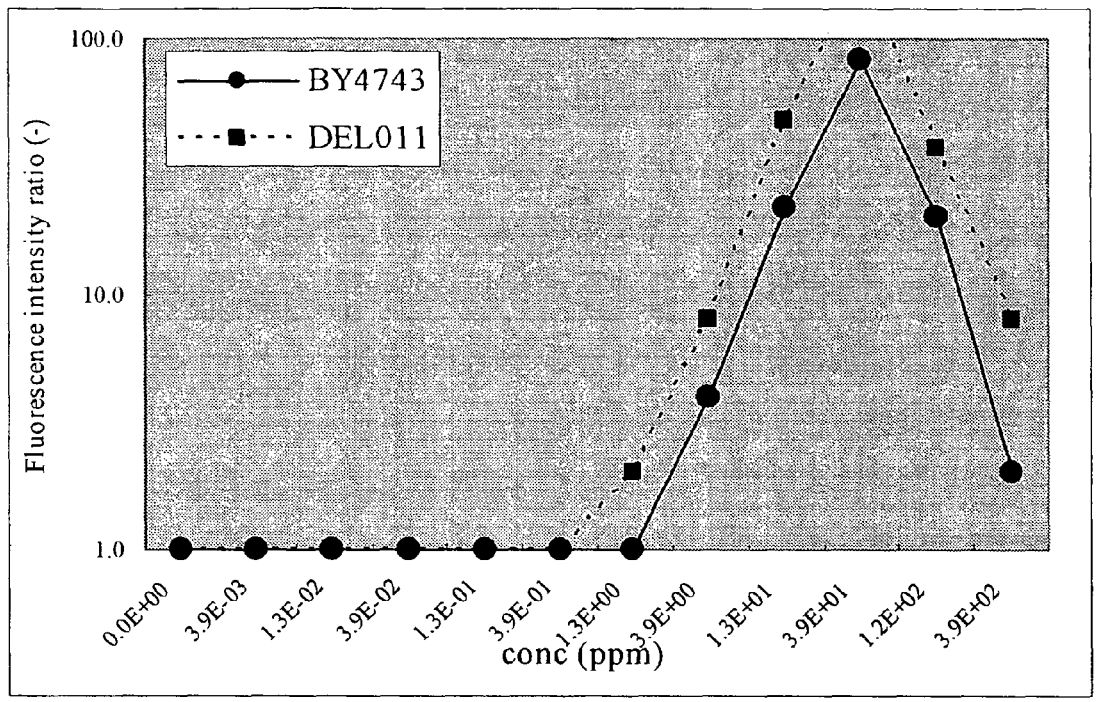
FIG. 1 is a graph showing a sensitivity to sodium metaarsenite in a gene-disrupted strain DEL011 transformed with a plasmid p-YPL171C.

One aspect of the present invention will be explained by referring to a yeast gene.

1) Selection of Gene-Disrupted Strain and Classification of Function Thereof

Among 4800 kinds of gene-disrupted strains of Yeast Deletion Homozygous Diploid (YKO Plate sets: Yeast Deletion Homozygous Diploid complete set, ResGen™, Invitrogen) used as a yeast gene-disrupted strain, 84 kinds of strains showing a better sensitivity to a chemical were selected (Example 1). Disrupted genes of 84 kinds of strains were classified according to classification of public database: MIPS (Munich Information center for Protein Sequences). Classification of MIPS classifies genes based on functions thereof, and the information can be easily obtained from the following URL: [[http://]]mips.gsf.de/genre/proj/yeast/searchCatalogFirstAction.do?style=catalog.xslt&table=FUNCTIONAL_CATEGORIES According to classification of MIPS, yeast genes are classified as shown in the following Table:

TABLE 1

| 01 | Metabolism |
|---|---|
| 01.01 | Amino acid metabolism |
| 01.02 | Nitrogen and sulfur metabolism |
| 01.03 | Nucleotide metabolism |
| 01.04 | Phosphate metabolism |
| 01.05 | C-compound and carbohydrate metabolism |
| 01.06 | Lipid, fatty acid and isoprenoid metabolism |
| 01.07 | Metabolism of vitamins, cofactors and prosthetic groups |
| 01.20 | Secondary metabolism |
| 02 | Energy |
| 02.01 | Glycolysis and Gluconeogenesis |
| 02.07 | Pentose-phosphate pathway |
| 02.10 | Tricarboxylic-acid pathway (citrate cycle, Krebs cycle, TCA cycle) |
| 02.11 | Electron transport and membrane-associated energy conservation |
| 02.13 | Respiration |
| 02.16 | Fermentation |
| 02.19 | Energy storage metabolism (e.g. glycogen, trehalose) |
| 02.22 | Glyoxylic acid cycle |
| 02.25 | Oxidation of fatty acid |
| 02.99 | Other energy generation activities |
| 03 | Cell cycle and DNA processing |
| 03.01 | DNA processing |
| 03.03 | Cell cycle |
| 03.99 | Other cell division and DNA synthesis activities |
| 04 | Transcription |
| 04.01 | rRNA transcription |
| 04.03 | tRNA transcription |
| 04.05 | mRNA transcription |
| 04.07 | RNA transport |
| 04.99 | Other transcription activities |
| 05 | Protein synthesis |
| 05.01 | Ribosome biosynthesis |
| 05.04 | Translation |
| 05.07 | Translational control |
| 05.10 | Aminoacyl-tRNA-synthases |
| 05.99 | Other protein synthesis activities |
| 06 | Protein fate (folding, modification, destination) |
| 06.01 | Protein folding and stabilization |
| 06.04 | Protein targeting, sorting and translocation |
| 06.07 | Protein modification |
| 06.10 | Assembly of protein complexes |
| 06.13 | Proteolysis |
| 06.99 | Other protein fate-associated activities |
| 08 | Intracellular transport and transport mechanism |
| 08.01 | Nuclear transport |
| 08.04 | Mitochondrial transport |
| 08.07 | Vesicular transport (Golgi network etc.) |
| 08.10 | Peroxisomal transport |
| 08.13 | Vacuolar transport |
| 08.16 | Extracellular transport, exocytosis and secretion |
| 08.19 | Cellulular import |
| 08.22 | Cytoskeleton-dependent transport |
| 08.99 | Other intracellular transport activities |
| 10 | Cell transmission/signal transmitting mechanism |
| 10.01 | Intracellular signaling |
| 10.05 | Transmembrane signal transmission |
| 11 | Cell rescue, defense and pathogenicity |
| 11.01 | Stress response |
| 11.07 | Detoxification |
| 11.10 | Degradation of foreign compounds |
| 11.99 | Other cell rescue activities |
| 13 | Intracellular environmental regulation interaction |
| 13.01 | Ionic homeostasis |
| 13.11 | Cell sensitivity and response |
| 14 | Cell fate |
| 14.01 | Cell growth/morphogenesis |
| 14.04 | Cell differentiation |
| 14.10 | Cell death |
| 14.20 | Cell aging |
| 29 | Transpositional element, virus and plasmid protein |
| 29.07 | Protein necessary for integrating or inhibiting transposon transfer |
| 29.99 | Other transpositional element, virus and plasmid protein |
| 30 | Cell tissue control |
| 30.01 | Cell wall |
| 30.02 | Plasma membrane |
| 30.03 | Cytoplasm |

TABLE 1-continued

| | | |
|---|---|---|
| 30.04 | Cytoskeleton | |
| 30.05 | Centrorsome | |
| 30.07 | Endoplasmic reticulum | |
| 30.08 | Golgi | |
| 30.09 | Intracellular transport vesicle | |
| 30.10 | Nucleus | |
| 30.16 | Mitochondria | |
| 30.19 | Peroxisome | |
| 30.22 | Endosome | |
| 30.25 | Vacuole and lysosome | |
| 30.99 | Other control of cell tissue | |
| 40 | Intracellular sorting | |
| 40.01 | Cell wall | |
| 40.02 | Plasma membrane | |
| 40.03 | Cytoplasm | |
| 40.04 | Cytoskeleton | |
| 40.05 | Centrosome | |
| 40.07 | Endoplasmic reticulum | |
| 40.08 | Golgi | |
| 40.09 | Intracellular transport vesicle | |
| 40.10 | Nucleus | |
| 40.16 | Mitochondria | |
| 40.19 | Peroxisome | |
| 40.22 | Endosome | |
| 40.25 | Vacuole and lysosome | |
| 40.27 | Extracellular/secretion protein | |
| 62 | Protein activity regulation | |
| 62.01 | Regulation mechanism | |
| 62.02 | Regulation target | |
| 63 | Element necessary for protein or cofactor having binding function (structural or catalytic) | |
| 63.01 | Protein binding | |
| 63.03 | Nucleic acid binding | |
| 63.09 | Lipid binding | |
| 67 | Transport promotion | |
| 67.01 | Channel/pore class transporter | |
| 67.04 | Ion transporter | |
| 67.07 | C-compound and carbohydrate transporter | |
| 67.10 | Amino acid transporter | |
| 67.11 | Peptide transporter | |
| 67.13 | Lipid transporter | |
| 67.16 | Nucleotide transporter | |
| 67.19 | Allantoin and allantoate transporter | |
| 67.21 | Vitamin/cofactor transporter | |
| 67.28 | Drug transporter | |
| 67.50 | Transport mechanism | |
| 67.99 | Other transport promotion | |
| 98 | Unclassified | |
| 99 | Unclassified protein | |

Eighty four kinds of selected strains exhibiting better sensitivity to a chemical were classified according to the aforementioned database: MIPS classification.

TABLE 2

Classification based on function
Chemical sensitivity Functional classification of genes of
84 gene-disrupted strains

| Function | No | Gene | MIPS classification | description |
|---|---|---|---|---|
| METABOLISM 01 | DEL003 | YGL026C | 01.01.01 | Tryptophan synthase |
| | DEL004 | YGR180C | 01.03.07 | Ribonucleotide reductase small subunit |
| | DEL009 | YDR127W | 01.01.01 | Arom pentafunctional enzyme |
| | DEL016 | YCR028C | 01.02.04 01.05.04 01.06.10 01.07.10 | Pantothenate permease |
| | DEL023 | YLR284C | 01.06.04 | Delta3-cis-delta2-trans-enoyl-CoA isomerase |
| | DEL028 | YOR221C | 01.06.07 | Malonyl-CoA:ACP transferase |
| | DEL031 | YAL021C | 01.05.04 | Transcriptional regulator |
| | DEL038 | YGL224C | 01.03.04 | Pyrimidine 5-nucleotidase |
| | DEL052 | YBL042C | 01.03.04 | Uridine permease |
| | DEL056 | YDR148C | 01.05.01 | 2-Oxoglutarate dehydrogenase complex E2 component |
| | DEL064 | YHL025W | 01.05.04 | Global transcription activator |
| | DEL073 | YLR307W | 01.05.01 | Sporulation-specific chitin deacetylase |
| | DEL078 | YLR345W | 01.05.04 | Similarity to Pfk26p and other 6-phosphofructo-2-kinases |
| | DEL079 | YLR354C | 01.05.01 | Transaldolase |
| | DEL082 | YPL129W | 01.04.04 01.05.04 | TFIIFsubunit (transcription initiation factor), 30 kD |
| | DEL083 | YPR060C | 01.01.01 | chorismate mutase |
| CELL CYCLE AND DNA PROCESSING 03 | DEL004 | YGR180C | 03.01.03 | ribonucleotide reductase small subunit |
| | DEL010 | YDR150W | 03.03.01 | nuclear migration protein |
| | DEL011 | YGL240W | 03.03.01 | component of the anaphase promoting complex |
| | DEL015 | YBL058W | 03.03.01 03.03.02 | potential regulatory subunit for Glc7p |
| | DEL019 | YIL036W | 03.01.03 | ATF/CREB activator |
| | DEL022 | YLR226W | 03.03.01 | divergent CDK-cyclin complex |
| | DEL048 | YLR381W | 03.03.04.05 | outer kinetochore protein |
| | DEL050 | YOR026W | 03.03.01 | cell cycle arrest protein |
| | DEL051 | YPL018W | 03.03.04.05 | outer kinetochore protein |
| | DEL054 | YBL063W | 03.03.01 | kinesin-related protein |
| | DEL057 | YDR363W-A | 03.03.01 | regulator of exocytosis and pseudohyphal differentiation |

TABLE 2-continued

Classification based on function
Chemical sensitivity Functional classification of genes of
84 gene-disrupted strains

| Function | No | Gene | MIPS classification | description |
|---|---|---|---|---|
| | DEL065 | YIR026C | 03.03.02 | Protein tyrosine phosphatase |
| | DEL070 | YLR234W | 03.03.01 | DNA topoisomerase III |
| | DEL080 | YMR032W | 03.03.03 | involved in cytokinesis |
| | DEL082 | YPL129W | 03.03.01 | TFIIF subunit (transcription initiation factor), 30 kD |
| TRANSCRIPTION 04 | DEL012 | YGR006W | 04.05.05.01 | U5 snRNA-associated protein |
| | DEL019 | YIL036W | 04.05.01.04 | ATF/CREB activator |
| | DEL021 | YKR082W | 04.07 | nuclear pore protein |
| | DEL022 | YLR226W | 04.05.01.04 | divergent CDK-cyclin complex |
| | DEL026 | YML112W | 04.05.01.04 | carboxy-terminal domain (CTD) kinase, gamma subunit |
| | DEL027 | YMR021C | 04.05.01.04 | metal binding activator |
| | DEL031 | YAL021C | 04.05.01.04 | transcriptional regulator |
| | DEL033 | YDR195W | 04.05.05 | RNA 3′-end formation protein |
| | DEL049 | YOL068C | 04.05.01.04 | silencing protein |
| | DEL055 | YBR279W | 04.05.01.04 | DNA-directed RNA polymerase II regulator |
| | DEL058 | YGL070C | 04.05.01.01 | DNA-directed RNA polymerase II, 14.2 KD subunit |
| | DEL059 | YGL071W | 04.05.01.04 | iron-regulated transcriptional repressor |
| | DEL060 | YGL222C | 04.05.05.03 | stimulates mRNA decapping |
| | DEL064 | YHL025W | 04.05.01.04 | global transcription activator |
| | DEL071 | YLR266C | 04.05.01.04 | weak similarity to transcription factors |
| | DEL082 | YPL129W | 04.05.01.01 | TFIIF subunit (transcription initiation factor), 30 kD |
| PROTEIN SYNTHESIS 05 | DEL015 | YBL058W | 05.07 | potential regulatory subunit for Glc7p |
| | DEL044 | YLR287C-A | 05.01 | 40S small subunit ribosomal protein |
| | DEL062 | YGR084C | 05.01 | mitochondrial ribosomal protein, small subunit |
| | DEL077 | YLR344W | 05.01 | 60S large subunit ribosomal protein |
| PROTEIN FATE (folding, modification, destination) 06 | DEL007 | YKL080W | 06.10 | H+-ATPase V1 domain 42 KD subunit, vacuolar |
| | DEL008 | YLR447C | 06.10 | H+-ATPase V0 domain 36 KD subunit, vacuolar |
| | DEL011 | YGL240W | 06.07 06.13.01 | component of the anaphase promoting complex |
| | DEL013 | YGR105W | 06.10 | ATPase assembly integral membrane protein |
| | DEL018 | YGL206C | 06.04 | clathrin heavy chain |
| | DEL020 | YKL119C | 06.10 | H+-ATPase assembly protein |
| | DEL034 | YDR414C | 06.04 06.07 | Putative transport protein of inner membranes |
| | DEL040 | YHR060W | 06.10 | vacuolar ATPase assembly protein |
| | DEL046 | YLR292C | 06.04 | ER protein-translocation complex subunit |
| | DEL047 | YLR306W | 06.07 | E2 ubiquitin-conjugating enzyme |
| | DEL061 | YGL227W | 06.13.04 | weak similarity to human RANBPM NP_005484.1 |
| | DEL063 | YGR270W | 06.13.01 | 26S proteasome subunit |
| CELLULAR TRANSPORT AND TRANSPORT MECHANISMS 08 | DEL000 | YPR036W | 08.13 | H+-ATPase V1 domain 54 KD subunit, vacuolar |
| | DEL002 | YDR027C | 08.07 | subunit of VP51-54 complex, required for protein sorting at the yeast late Golgi |
| | DEL006 | YHR039C-A | 08.13 | H+-transporting ATPase V0 domain 13 KD subunit, vacuolar |
| | DEL007 | YKL080W | 08.13 | +-ATPase V1 domain 42 KD subunit, vacuolar |
| | DEL008 | YLR447C | 08.13 | H+-ATPase V0 domain 36 KD subunit, vacuolar |
| | DEL018 | YGL206C | 08.19 | clathrin heavy chain |
| | DEL021 | YKR082W | 08.01 | nuclear pore protein |
| | DEL046 | YLR292C | 08.99 | ER protein-translocation complex subunit |
| | DEL054 | YBL063W | 08.22 | kinesin-related protein |

TABLE 2-continued

Classification based on function
Chemical sensitivity Functional classification of genes of
84 gene-disrupted strains

| Function | No | Gene | MIPS classification | description |
|---|---|---|---|---|
| 11.07 . . . detoxification | DEL014 | YJR104C | 11.07 | copper-zinc superoxide dismutase |
| | DEL027 | YMR021C | 11.01 | metal binding activator |
| 13 . . . REGULATION OF/ INTERACTION WITH CELLULAR ENVIRONMENT | DEL000 | YPR036W | 13.01.01.03 | H+-ATPase V1 domain 54 KD subunit, vacuolar |
| | DEL006 | YHR039C-A | 13.01.01.03 | H+-transporting ATPase V0 domain 13 KD subunit, vacuolar |
| | DEL007 | YKL080W | 13.01.01.01 | H+-ATPase V1 domain 42 KD subunit, vacuolar |
| | DEL008 | YLR447C | 13.01.01.03 | H+-ATPase V0 domain 36 KD subunit, vacuolar |
| | DEL059 | YGL071W | 13.01.01.01 | iron-regulated transcriptional repressor |
| | DEL065 | YIR026C | 13.11.03.01 | protein tyrosine phosphatase |
| 14 . . . CELL FATE | DEL001 | YDL151C | 14.04.03.01 | involved in bipolar bud site selection |
| | DEL015 | YBL058W | 14.04.03.01 | potential regulatory subunit for Glc7p |
| | DEL021 | YKR082W | 14.04.03.05 | potential regulatory subunit for Glc7p |
| | DEL032 | YDL151C | 14.04.03.01 | involved in bipolar bud site selection |
| | DEL049 | YOL068C | 14.04.03.03 | silencing protein |
| | DEL057 | YDR363W-A | 14.04.03.01 | regulator of exocytosis and pseudohyphal differentiation |
| | DEL064 | YHL025W | 14.04.03.03 | global transcription activator |
| | DEL065 | YIR026C | 14.04.03.05 | protein tyrosine phosphatase |
| | DEL073 | YLR307W | 14.04.03.05 | sporulation-specific chitin deacetylase |
| | DEL080 | YMR032W | 14.01 14.04.03.01 | involved in cytokinesis |
| | DEL082 | YPL129W | 14.04.03.03 | 30 kD: TFIIF subunit (transcription initiation factor), 30 kD |
| 30 . . . CONTROL OF CELLULAR ORGANIZATION | DEL002 | YDR027C | 30.01 30.04.03 | subunit of VP51-54 complex, required for protein sorting at the yeast late Golgi |
| | DEL034 | YDR414C | 30.01 | Putative transport protein of inner membranes |
| | DEL048 | YLR381W | 30.10.03 | outer kinetochore protein |
| | DEL062 | YGR084C | 30.16 | mitochondrial ribosomal protein, small subunit |
| | DEL080 | YMR032W | 30.04 | involved in cytokinesis |
| 67 . . . TRANSPORT FACILITATION | DEL000 | YPR036W | 67.04.01.02 67.50.22 | H+-ATPase V1 domain 54 KD subunit, vacuolar |
| | DEL005 | YHR026W | 67.04.01.02 67.50.22 | H+-ATPase 23 KD subunit, vacuolar |
| | DEL006 | YHR039C-A | 67.04.01.02 67.50.22 | H+-transporting ATPase V0 domain 13 KD subunit, vacuolar |
| | DEL007 | YKL080W | 67.04.01.02 67.50.22 | H+-ATPase V1 domain 42 KD subunit, vacuolar |
| | DEL008 | YLR447C | 67.04.01.02 67.50.22 | H+-ATPase V0 domain 36 KD subunit, vacuolar |
| | DEL016 | YCR028C | 67.21 | Pantothenate permease |
| | DEL046 | YLR292C | 67.99 | ER protein-translocation complex subunit |
| UNCLASSIFIED PROTEINS | DEL053 | YBL056W | 98. | ser/thr protein phosphatase PP2C |
| | DEL017 | YDR149C | 99. | |
| | DEL024 | YLR285W | 99. | weak similarity to *A. thaliana* hypothetical protein |
| | DEL025 | YLR311C | 99. | weak similarity to *S. tarentolae* cryptogene protein G4 |
| | DEL029 | YOR331C | 99. | |

TABLE 2-continued

Classification based on function
Chemical sensitivity Functional classification of genes of
84 gene-disrupted strains

| Function | No | Gene | MIPS classification | description |
|---|---|---|---|---|
| | DEL030 | YPR123C | 99. | |
| | DEL035 | YDR525W-A | 99. | PMP3/SNA1 (similarity) |
| | DEL036 | YDR539W | 99. | similarity to E. coli hypothetical 55.3 kDa protein in rfah-rfe intergenic region |
| | DEL037 | YDR540C | 99. | similarity to E. coli unknown gene |
| | DEL039 | YGL246C | 99. | weak similarity to C. elegans dom-3 protein |
| | DEL041 | YJL204C | 99. | involved in recycling of the SNARE Snc1p |
| | DEL042 | YLR282C | 99. | |
| | DEL043 | YLR287C | 99. | weak similarity to S. pombe hypothetical protein SPAC22E12 |
| | DEL045 | YLR290C | 99. | similarity to hypothetical protein SPCC1840.09 S. pombe |
| | DEL066 | YJL188C | 99. | |
| | DEL067 | YJL192C | 99. | facilitates ER export of the yeast plasma membrane [H+]ATPase, Pma1 |
| | DEL068 | YJL211C | 99. | |
| | DEL069 | YKL037W | 99. | weak similarity to C. elegans ubc-2 protein |
| | DEL072 | YLR283W | 99. | weak similarity to Smc2p |
| | DEL074 | YLR312C | 99. | hypothetical protein |
| | DEL075 | YLR315W | 99. | weak similarity to rat apolipoprotein A-IV |
| | DEL076 | YLR320W | 99. | hypothetical protein |
| | DEL081 | YPL030W | 99. | similarity to C. elegans hypothetical protein |

Further, gene-disrupted strains exhibiting sensitivity to 7 or more kinds of chemicals among 12 kinds of chemicals which were tested in the following Examples are classified based on function, as in Table 3.

TABLE 3

Classification depending on function

| Function | Number of gene-disrupted strains |
|---|---|
| Metabolism-amino acid metabolism (01.01) | 2 |
| Metabolism-C-compound and carbohydrate metabolism (01.05) | 1 |
| Lipid, fatty acid and isoprenoid metabolism (01.06) | 3 |
| Cell cycle and DNA processing-DNA processing (03.01) | 2 |
| Cell cycle and DNA processing-cell cycle (03.03) | 4 |
| Transcription-mRNA transcription (04.05) | 5 |
| Protein fate (folding, modification, destination)-protein modification (06.07) | 1 |
| Protein fate (folding, modification, destination)-protein complex assembling (06.10) | 4 |
| Intracellular transport and transport mechanism-vacuolar transport (08.13) | 3 |
| Intracellular environmental regulation/interaction-ionic homeostasis (13.01) | 3 |
| Cell fate-cell differentiation (14.04) | 3 |
| Transport promotion-ion transporter (67.04) | 4 |
| Transport promotion-transport mechanism (67.50) | 4 |
| Unclassified protein (99) | 4 |

When the same gene has overlapped functions, it was counted repeatedly. Particularly, there were many overlaps in intracellular transport and transport mechanism-vacuolar transport (08.13), intracellular environmental regulation/interaction-ionic homeostasis (13.01), transport promotion-ion transporter (67.04), and transport promotion-transport regulation (67.50).

In particular, genes are overlapped in intracellular transport and transport mechanism-vacuole transport (08.13), intracellular environmental regulation/interaction-ionic homeostasis (13.01), transport promotion-ion transporter (67.04), and transport promotion-transport mechanism (67.50) and, since 50% of higher 10 genes were in this category, it was confirmed by this study that a vacuole plays an important role in detoxificating a chemical. In addition, it was seen that transcription-mRNA transcription (04.05), cell cycle and DNA synthesis-cell cycle (03.03), cell fate-cell differentiation (14.04), cell cycle and DNA synthesis-DNA synthesis (03.01), protein fate (folding, modification, destination)-protein complex assembling (06.10), metabolism-amino acid biosynthesis (01.01), metabolism-C-bond, carbohydrate metabolism (01.05), lipid, fatty acid, isoprenoid metabolism (01.06) are also involved in response to a chemical. Further, usefulness of genes whose functions were not known was confirmed.

In the present invention, a microorganism other than yeast can be used. Herein, as a microorganism, any of an animal cell derived from human, mouse and other mammal, and an established strain of an animal cell, and cells of fishes, a nematode and the like, an insect cell, a eukaryote cell such as yeast and the like, and a bacterial cell such as Escherichia coli may be used. And, when a gene-disrupted strain of a gene corresponding to a gene having function found in the yeast utilizing known database is made by the known procedure, it can be utilized in the method of the present invention. Particularly, genes corresponding to function described as "description" in classification based on function in Table 2 can be utilized as a subject of a disrupted gene in a disrupted strain.

(2) Use of Selected Gene-Disrupted Strains

By destructing a particular gene, a microorganism exhibits sensitivity or resistance to a chemical in some cases.

In the present invention, the "gene-disrupted strain" includes a monoploid gene-disrupted strain, a homozygous diploid gene-disrupted strain and a heterozygous diploid gene-disrupted strain. A yeast cell can form a diploid by mating between an α-type cell and an a-type cell which are a monoploid. A homozygous diploid gene-disrupted strain is a strain in which genes disrupted in α and a are the same and, on the other hand, a heterozygous diploid gene-disrupted strain refers to a strain in which a gene disrupted in α and a gene disrupted in a are different, and a strain in which only a gene in α or a is disrupted. The number of genes to be disrupted is not limited to one, but a plurality of genes among those listed above may be disrupted.

In the present invention, a gene-disrupted strain having an improved sensitivity to a chemical is selected, and utilized for assaying a chemical. The presence of a chemical is assayed utilizing, as an index, cell response to a chemical of a gene-disrupted strain. Cell response to a chemical shows life or death of a cell, and/or proliferation ability an aspiration amount, enzyme activity and/or a change in gene expression.

Herein, "life or death of a cell" can be measured and assessed by a ratio of a living cell or an ATP amount, "proliferation ability" by a ratio of increase in a cell number, "aspiration amount" by a consumed amount of oxygen, "enzyme activity" by enzyme activity originally possessed by an index cell and "change in gene expression" by a RNA amount or a mRNA amount. In addition, in the present invention, as measurement of a change in particular gene expression, a method of measuring an expression amount of a particular gene measured by a Northern blotting method (Molecular Biology of Cell, second edition, published by Kyouiku-sha Co., Ltd. in 1990, pp. 189-191) or an reporter·gene·assay method can be also utilized.

Among them, a method of measuring life or death of a cell, proliferation ability, an aspiration amount, or a change in expression of a particular gene is a simple procedure and suitable in bioassay. The reporter·gene·assay is procedure of measuring activity of a particular gene as a mark for investigating function of a gene laying stress on transcription activity, and includes a promoter assay method. The promoter assay method is a method of ligating operatively a polynucleotide encoding a marker protein to the polynucleotide sequence of a promoter of a gene and indirectly measuring expression of a gene (Barelle C J, Manson C L, MacCallum D M, Odds F C, Gow Na, Brown A J.: GFP as a quantitative reporter of gene regulation in *Candida albicans*. Yeast 2004 March; 21(4):333-40).

A gene-disrupted strain which can be suitably used in chemical detection in the present invention using cell response as an index includes the following strains in which a gene is disrupted:
YPR036W, YDL151C, YDR027C, YGL026C, YGR180C, YHR026W, YHR039C-A, YKL080W, YLR447C, YDR127W, YDR150W, YGL240W, YGR006W, YGR105W, YJR104C, YBL058W, YCR028C, YDR149C, YGL206C, YIL036W, YKL119C, YKR082W, YLR226W, YLR284C, YLR285W, YLR311C, YML112W, YMR021C, YOR221C, YOR331C, YPR123C, YAL021C, YDL151C, YDR195W, YDR414C, YDR525W-A, YDR539W, YDR540C, YGL224C, YGL246C, YHR060W, YJL204C, YLR282C, YLR287C, YLR287C-A, YLR290C, YLR292C, YLR306W, YLR381W, YOL068C, YOR026W, YPL018W, YBL042C, YBL056W, YBL063W, YBR279W, YDR148C, YDR363W-A, YGL070C, YGL071W, YGL222C, YGL227W, YGR084C, YGR270W, YHL025W, YIR026C, YJL188C, YJL192C, YJL211C, YKL037W, YLR234W, YLR266C, YLR283W, YLR307W, YLR312C, YLR315W, YLR320W, YLR344W, YLR345W, YLR354C, YMR032W, YPL030W, YPL129W and YPR060C.

When a change in gene expression is selected as cell response to a chemical and the gene change is measured by reporter·gene·assay, plasmids which can be utilized in reporter gene assay are described in WO03/01872. In one aspect of the present invention, a plasmid containing a polynucleotide in which a polynucleotide encoding a marker protein is operatively connected to a polynucleotide sequence containing a promoter of a yeast gene described in WO 03/01872 is utilized.

Preferable combinations of a gene-disrupted strain which can be suitably used, and a chemical which can be detected are as follows:

TABLE 4

Correspondence of gene disrupted strain and chemical

| Disrupted gene | Number of chemical | Kind of Chemical |
|---|---|---|
| YPR036W | 10 | methylmercury chloride, sodium arsenite, nickelous chloride, a potassium dichromate triphenyltin = chloride, mercuric chloride, lead chloride, SDS-DMSO, zinc chloride |
| YDL151C | 9 | sodium arsenite, nickelous chloride, potassium dichlomate, triphenyltin = chloride, mercuric chloride, lead chloride, SDS DMSO, zinc chloride |
| YDR027C | 9 | sodium arsenite, nickelous chloride, triphenyltin = chloride, mercuric chloride, lead chloride, SDS, DMSO, zinc chloride |
| YGL026C | 9 | sodium arsenite, nickelous chloride, triphenyltin = chloride, mercuric chloride, copper sulfate, lead chloride, SDS, DMSO, zinc chloride |
| YGR180C | 9 | methylmercury chloride, sodium arsenite, potassium dichromate triphenyltin = chloride, mercuric chloride, lead chloride, SDS, DMSO, zinc chloride |

TABLE 4-continued

Correspondence of gene disrupted strain and chemical

| Disrupted gene | Number of chemical | Kind of Chemical |
|---|---|---|
| YHR026W | 9 | methylmercury chloride, sodium arsenite, nickelous chloride, potassium dichromate triphenyltin = chloride, mercuric chloride, lead chloride, DMSO, zinc chloride |
| YHR039C-A | 9 | methylmercury chloride, sodium arsenite, potassium dichromate, triphenyltin = chloride, mercuric chloride, lead chloride, SDS, DMSO, zinc chloride |
| YKL080W | 9 | methylmercury chloride, sodium arsenite, nickelous chloride, a triphenyltin = chloride, mercuric chloride, lead chloride, SDS, DMSO, zinc chloride |
| YLR447C | 9 | sodium arsenite, nickelous chloride, potassium dichromate, triphenyltin = chloride, mercuric chloride, lead chloride, SDS, DMSO, zinc chloride |
| YDR127W | 8 | nickelous chloride, triphenyltin = chloride, mercuric chloride, copper sulfate, lead chloride, SDS, DMSO, zinc chloride |
| YDR150W | 8 | methylmercury chloride, sodium arsenite, potassium dichromate, trilphenyltin = chloride, mercuric chloride, copper sulfate, potassium cyanide, zinc chloride |
| YGL240W | 8 | methylmercury chloride, triphenyltin = chloride, mercuric chloride, coppersulfate, potassium cyanide, SDS DMSO, zinc chloride |
| YGR006W | 8 | methylmercury chloride, triphenyltin = chloride, mercuric chloride, coppersulfate, potassium cyanide, lead chloride, SDS, zinc chloride |
| YGR105W | 8 | nickelous chloride, potassium dichromate, triphenyltin = chloride, mercuric chloride, lead chloride, SDS, DMSO, zinc chloride |
| YJR104C | 8 | methylmercury chloride, soium arsenite, potassium dichromate chloride, a triphenyltin = chloride, mercuric chloride, SDS DMSO, zinc chloride |
| YBL058W | 7 | sodium arsenite, triphenyltin = chloride, mercuric chloride, copper sulfate, lead chloride, DMSO, zinc chloride |
| YCR028C | 7 | methylmercury chloride, triphenyltin = chloride, mercuric chloride, copper sulfate, SDS, DMSO, zinc chloride |
| YDR149C | 7 | methylmercury chloride, sodium arsenite, potassium dichromate, mercuric chloride, potassium cyanide, lead chloride, zinc chloride |
| YGL206C | 7 | sodium arsenite, nickelous chloride, potassium dichromate, mercuric chloride, lead chloride, SDS, DMSO |
| YIL036W | 7 | methylmercury chloride, sodium arsenite, triphenyltin = chloride, mercuric chloride, copper sulfate, lead chloride, zinc chloride |
| YKL119C | 7 | sodium arsenite, potassium dichromate, triphenyltin = chloride, mercuric chloride, lead chloride, SDS, zinc chloride |
| YKR082W | 7 | potassium dichromate, triphenyltin = chloride, mercuric chloride, potassium cyanide, lead chloride, DMSO, zinc chloride |
| YLR226W | 7 | methylmercury chloride, potassium dichromate, triphenyltin = chloride, mercuric chloride, copper sulfate, lead chloride, zinc chloride |
| YLR284C | 7 | triphenyltin = chloride, mercuric chloride, copper sulfate, lead chloride, SDS, DMSO, zinc chloride |
| YLR285W | 7 | methylmercury chloride, triphenyltin = chloride, coppersulfate, lead chloride, SDS, DMSO, zinc chloride |
| YLR311C | 7 | methylmercury chloride, triphenyltin = chloride, mercuric chloride, copper sulfate, lead chloride, DMSO, zinc chloride |
| YML112W | 7 | methylmercury chloride, sodium arsenite, nickelous chloride, potassium dichromate, triphenyltin = chloride, mercuric chloride, DMSO |
| YMR021C | 7 | methylmercury chloride, sodium arsenite, triphenyltin = chloride, mercuric chloride, SDS, DMSO, zinc chloride |

TABLE 4-continued

Correspondence of gene disrupted strain and chemical

| Disrupted gene | Number of chemical | Kind of Chemical |
|---|---|---|
| YOR221C | 7 | methylmercury chloride, sodium arsenite, mercuric chloride, coper sulfate, lead chloride, DMSO, zinc chloride |
| YOR331C | 7 | nickelous chloride, potassium dichromate, triphenyltin = chloride, mercuric chloride, lead chloride, SDS, zinc chloride |
| YPR123C | 7 | methylmercury chloride, sodium arsenite, nickelous chloride, triphenyltin = chloride, mercuric chloride, DMSO, zinc chloride |
| YAL021C | 6 | sodium arsenite, potassium dichromate, triphenyltin = chloride, mercuric chloride, copper sulfate, lead chloride |
| YDL151C | 6 | methylmercury chloride, sodium arsenite, mercuric chloride, copper sulfate, lead chloride, SDS |
| YDR195W | 6 | sodium arsenite, potassium dichromate, triphenyltin = chloride, mercuric chloride, potassium cyanide, DMSO |
| YDR414C | 6 | potassium dichromate, triphenyltin = chloride, mercuric chloride, copper sulfate, lead chloride, zinc chloride |
| YDR525W-A | 6 | triphenyltin = chloride, copper sulfate, lead chloride, SDS, DMSO, zinc chloride |
| YDR539W | 6 | triphenyltin = chloride, copper sulfate, lead chloride, SDS, DMSO, zinc chloride |
| YDR540C | 6 | triphenyltin = chloride, mercuric chloride, copper sulfate, SDS, DMSO, zinc chloride |
| YGL224C | 6 | methylmercury chloride, triphenyltin = chloride, copper sulfate, potassium cyanide, lead chloride, zinc chloride |
| YGL246C | 6 | methylmercury chloride, triphenyltin = chloride, lead chloride, SDS, DMSO, zinc chloride |
| YHR060W | 6 | methylmercury chloride, triphenyltin = chloride, mercuric chloride, lead chloride, DMSO, zinc chloride |
| YJL204C | 6 | triphenyltin = chloride, mercuric chloride, copper sulfate, lead chloride, DMSO, zinc chloride |
| YLR282C | 6 | triphenyltin = chloride, mercuric chloride, lead chloride,, SDS, DMSO, zinc chloride |
| YLR287C | 6 | triphenyltin = chloride, mercuric chloride, copper sulfate,, SDS, DMSO, zinc chloride |
| YLR287C-A | 6 | triphenyltin = chloride, mercuric chloride, copper sulfate, lead chloride, SDS, DMSO |
| YLR290C | 6 | triphenyltin = chloride, mercuric chloride, copper sulfate, lead chloride, SDS, zinc chloride |
| YLR292C | 6 | mercuric chloride, copper sulfate, lead chloride, SDS, DMSO, zinc chloride |
| YLR306W | 6 | methylmercury chloride, triphenyltin = chloride, mercuric chloride, copper sulfate, lead chloride, zinc chloride |
| YLR381W | 6 | triphenyltin = chloride, mercuric chloride, copper sulfate, lead chloride, DMSO, zinc chloride |
| YOL068C | 6 | methylmercury chloride, potassium dichromate, triphenyltin = chloride, mercuric chloride, copper sulfate, lead chloride |
| YOR026W | 6 | nickelous chloride, triphenyltin = chloride, mercuric chloride, lead chloride, SDS, DMSO |
| YPL018W | 6 | triphenyltin = chloride, mercuric chloride, copper sulfate, potassium cyanide, lead chloride, DMSO |
| YBL042C | 5 | mercuric chloride, copper sulfate, lead chloride, DMSO, zinc chloride |
| YBL056W | 5 | potassium dichromate, copper sulfate, lead chloride, DMSO, zinc chloride |
| YBL063W | 5 | triphenyltin = chloride, mercuric chloride, lead chloride, DMSO, zinc chloride |
| YBR279W | 5 | methylmercury chloride, potassium dichromate, mercuric chloride, SDS, DMSO |
| YDR148C | 5 | potassium dichromate, triphenyltin = chloride, mercuric chloride, copper sulfate, lead chloride |
| YDR363W-A | 5 | triphenyltin = chloride, copper sulfate, lead chloride, DMSO, zinc chloride |
| YGL070C | 5 | triphenyltin = chloride, mercuric chloride, potassium cyanide, SDS, DMSO |
| YGL071W | 5 | nickelous chloride, potassium dichromate, triphenyltin = chloride, mercuric chloride, zinc chloride |

TABLE 4-continued

Correspondence of gene disrupted strain and chemical

| Disrupted gene | Number of chemical | Kind of Chemical |
|---|---|---|
| YGL222C | 5 | methylmercury chloride, sodium arsenite, triphenyltin = chloride, copper sulfate, zinc chloride |
| YGL227W | 5 | mercuric chloride, copper sulfate, potassium cyanide, lead chloride, zinc chloride |
| YGR084C | 5 | copper sulfate, lead chloride, SDS, DMSO, zinc chloride |
| YGR270W | 5 | sodium arsenite, potassium dichromate, mercuric chloride, copper sulfate, zinc chloride |
| YHL025W | 5 | sodium arsenite, potassium dichromate,, triphenyltin = chloride, mercuric chloride, DMSO |
| YIR026C | 5 | sodium arsenite, triphenyltin = chloride, lead chloride, SDS, zinc chloride |
| YJL188C | 5 | mercuric chloride, copper sulfate, lead chloride, DMSO, zinc chloride |
| YJL192C | 5 | triphenyltin = chloride, mercuric chloride, copper sulfate, lead chloride, DMSO |
| YJL211C | 5 | methylmercury chloride, triphenyltin = chloride, copper sulfate, DMSO, zinc chloride |
| YKL037W | 5 | sodium arsenite, triphenyltin = chloride, mercuric chloride, DMSO, zinc chloride |
| YLR234W | 5 | nickelous chloride, mercuric chloride, lead chloride, SDS, DMSO |
| YLR266C | 5 | nickelous chloride, triphenyltin = chloride, mercuric chloride, copper sulfate, lead chloride |
| YLR283W | 5 | copper sulfate, lead chloride, SDS, DMSO, zinc chloride |
| YLR307W | 5 | triphenyltin = chloride, mercuric chloride, lead chloride, DMSO, zinc chloride |
| YLR312C | 5 | triphenyltin = chloride, mercuric chloride, copper sulfate, lead chloride, zinc chloride |
| YLR315W | 5 | methylmercury chloride, sodium arsenite, potassium dichromate, triphenyltin = chloride, potassium cyanide |
| YLR320W | 5 | sodium arsenite, potassium dichromate, triphenyltin = chloride, potassium cyanide, zinc chloride |
| YLR344W | 5 | mercuric chloride, copper sulfate, SDS, DMSO, zinc chloride |
| YLR345W | 5 | copper sulfate, lead chloride, SDS, DMSO, zinc chloride |
| YLR354C | 5 | mercuric chloride, lead chloride, SDS, DMSO, zinc chloride |
| YMR032W | 5 | potassium dichromate, triphenyltin = chloride, mercuric chloride, copper sulfate, lead chloride |
| YPL030W | 5 | triphenyltin = chloride, mercuric chloride, copper sulfate, potassium cyanide, SDS |
| YPL129W | 5 | methylmercury chloride, potassium dichromate, triphenyltin = chloride, lead chloride, zinc chloride |
| YPR060C | 5 | nickelous chloride, mercuric chloride, lead chloride, SDS, DMSO |

(3) Kit

A kit of the present invention contains a container containing a dried product, for example, a lyophilized product, a L-dried product or a frozen product of the gene-disrupted strain, a culturing medium and the like.

As the culturing medium, a medium having a suitable composition for a gene-disrupted strain to be used, is used.

(4) Composition

As another aspect, the present invention provides a composition containing a gene-disrupted strain of a microorganism for detecting whether a chemical is present in a test specimen or not. Typically, a present composition is the culturing medium containing the gene-disrupted strain.

EXAMPLES

The present invention will be explained in more detailed below by Examples, but the present invention is not limited to these Examples.

Example 1

Test of chemical sensitivity of gene-disrupted strain using growth inhibition in chemical plate as index.

a) Method

As a yeast gene-disrupted strain, Yeast Deletion Homozygous Diploid (YKO Plate sets: Yeast Deletion Homozygous Diploid complete set, ResGen™, Invitrogen) was used. A parent strain of this gene-disrupted strain is *Saccharomyces crevisiae* BY4743. Among 6000 kinds of yeast gene-disrupted strains, a plurality of disrupted strains which can be chemical-sensitive are selected. Some of actual gene-disrupted strains can not be grown depending on a gene when it is defective. Then, as subject of the present experiment, about 4800 kinds of gene-disrupted strains which can be grown as Homozygous diploids were selected.

The frozen and stored gene-disrupted strain was grown to the steady state by shaking-culturing at 25° C. on a YPD medium (yeast extract 1%, polypeptone 2%, glucose 2%). Cells in the steady state were diluted 10000-fold with the same medium, and each 1.5 μL of diluted cells were added dropwise to a chemical-containing agar medium (Chemical Plate), and formation of colonies was observed after three days. Chemical plate was made by adding a chemical to a YPD agar medium (yeast extract 1%, polypeptone 2%, glucose 2%, agar 2%) to a final concentration shown in Table 5.

TABLE 5

Chemicals in sensitivity experiment of gene-disrupted strain by chemical plate

| No | Chemical | Concentration | | |
|---|---|---|---|---|
| C001P | Methylmercury chloride | 0.07 μM | 0.2 μM | 0.6 μM |
| C002P | Sodium arsenite | 0.3 mM | 1 mM | 3 mM |
| C003P | Nickelous chloride | 1 mM | 3 mM | 9 mM |
| C004P | Potassium dichromate | 0.3 mM | 1 mM | 3 mM |
| C005P | Triphenyltin = chloride | 0.007 mM | 0.02 mM | 0.06 mM |
| C006P | Mercuric chloride | 0.033 mM | 0.1 mM | 0.3 mM |
| C007P | Copper sulfate | 2.67 mM | 8 mM | 24 mM |
| C008P | Potassium cyanide | 6 mM | 18 mM | 54 mM |
| C009P | Lead chloride | 0.67 mM | 2 mM | 6 mM |
| C010P | SDS | 0.003% | 0.01% | 0.03% |
| C011P | DMSO | 1% | 3% | 9% |
| C012P | Zinc chloride | 3.3 mM | 10 mM | 30 mM | b) Results

Experiment of chemical sensitivity was performed for about 4800 kinds of gene-disrupted strains. From test results, the number of chemicals to which sensitivity was exhibited was calculated for each gene-disrupted strain, and summarized in Table 6. Herein, exhibiting sensitivity refers to growth inhibition of a parent strain at two or more concentrations. Two or more concentrations means that when growth was compared at different three concentrations for each chemical as shown in Table 5, growth is worse, or growth is not seen at two or more concentrations as compared with growth of a parent strain. For growth of a cell, life or death of a cell, and proliferation ability (growth number or growing rate) were used as an index.

TABLE 6

Number of gene-disrupted strains exhibiting sensitivity to chemical

| Number of chemicals to which sensitivity was exhibited | Number of gene-disrupted strains |
|---|---|
| 0 | 4149 |
| 1 | 348 |
| 2 | 135 |
| 3 | 59 |
| 4 | 61 |
| 5 | 32 |
| 6 | 21 |
| 7 | 16 |
| 8 | 6 |
| 9 | 8 |
| 10 | 1 |
| 11 | 0 |
| 12 | 0 |

Among about 4800 of gene-disrupted strains, the number of gene-disrupted strains exhibiting sensitivity to 10 kinds of chemicals is 1, the number is 8 to 9 kinds of chemicals, 6 to 8 kinds of chemicals, 16 to 7 kinds of chemicals, 21 to 6 kinds of chemicals, 32 to 5 kinds of chemicals, 61 to 4 kinds of chemicals, 59 to 3 kinds of chemicals, 135 to 2 kinds of chemicals, 348 to 1 kind of chemical, and the number of strains exhibiting no sensitivity to chemicals was 4149. Particularly, gene-disrupted strains exhibiting sensitivity to 5 or more chemicals are shown in Table 7.

TABLE 7

Gene-disrupted strains exhibiting sensitivity to 5 or more chemicals

| Name of disrupted strain | Disrupted gene | Number of chemicals exhibiting growth inhibition at 2 or more concentrations |
|---|---|---|
| DEL000 | YPR036W | 10 |
| DEL001 | YDL151C | 9 |
| DEL002 | YDR027C | 9 |
| DEL003 | YGL026C | 9 |
| DEL004 | YGR180C | 9 |
| DEL005 | YHR026W | 9 |
| DEL006 | YHR039C-A | 9 |
| DEL007 | YKL080W | 9 |
| DEL008 | YLR447C | 9 |
| DEL009 | YDR127W | 8 |
| DEL010 | YDR150W | 8 |
| DEL011 | YGL240W | 8 |
| DEL012 | YGR006W | 8 |
| DEL013 | YGR105W | 8 |
| DEL014 | YJR104C | 8 |
| DEL015 | YBL058W | 7 |
| DEL016 | YCR028C | 7 |
| DEL017 | YDR149C | 7 |
| DEL018 | YGL206C | 7 |
| DEL019 | YIL036W | 7 |
| DEL020 | YKL119C | 7 |
| DEL021 | YKR082W | 7 |
| DEL022 | YLR226W | 7 |
| DEL023 | YLR284C | 7 |
| DEL024 | YLR285W | 7 |
| DEL025 | YLR311C | 7 |
| DEL026 | YML112W | 7 |
| DEL027 | YMR021C | 7 |
| DEL028 | YOR221C | 7 |
| DEL029 | YOR331C | 7 |
| DEL030 | YPR123C | 7 |
| DEL031 | YAL021C | 6 |
| DEL032 | YDL151C | 6 |
| DEL033 | YDR195W | 6 |
| DEL034 | YDR414C | 6 |
| DEL035 | YDR525W-A | 6 |
| DEL036 | YDR539W | 6 |
| DEL037 | YDR540C | 6 |
| DEL038 | YGL224C | 6 |
| DEL039 | YGL246C | 6 |
| DEL040 | YHR060W | 6 |
| DEL041 | YJL204C | 6 |
| DEL042 | YLR282C | 6 |
| DEL043 | YLR287C | 6 |
| DEL044 | YLR287C-A | 6 |
| DEL045 | YLR290C | 6 |
| DEL046 | YLR292C | 6 |
| DEL047 | YLR306W | 6 |
| DEL048 | YLR381W | 6 |
| DEL049 | YOL068C | 6 |
| DEL050 | YOR026W | 6 |
| DEL051 | YPL018W | 6 |
| DEL052 | YBL042C | 5 |
| DEL053 | YBL056W | 5 |
| DEL054 | YBL063W | 5 |
| DEL055 | YBR279W | 5 |
| DEL056 | YDR148C | 5 |
| DEL057 | YDR363W-A | 5 |
| DEL058 | YGL070C | 5 |
| DEL059 | YGL071W | 5 |
| DEL060 | YGL222C | 5 |
| DEL061 | YGL227W | 5 |

TABLE 7-continued

Gene-disrupted strains exhibiting sensitivity to 5 or more chemicals

| Name of disrupted strain | Disrupted gene | Number of chemicals exhibiting growth inhibition at 2 or more concentrations |
|---|---|---|
| DEL062 | YGR084C | 5 |
| DEL063 | YGR270W | 5 |
| DEL064 | YHL025W | 5 |
| DEL065 | YIR026C | 5 |
| DEL066 | YJL188C | 5 |
| DEL067 | YJL192C | 5 |
| DEL068 | YJL211C | 5 |
| DEL069 | YKL037W | 5 |
| DEL070 | YLR234W | 5 |
| DEL071 | YLR266C | 5 |
| DEL072 | YLR283W | 5 |
| DEL073 | YLR307W | 5 |
| DEL074 | YLR312C | 5 |
| DEL075 | YLR315W | 5 |
| DEL076 | YLR320W | 5 |
| DEL077 | YLR344W | 5 |
| DEL078 | YLR345W | 5 |
| DEL079 | YLR354C | 5 |
| DEL080 | YMR032W | 5 |
| DEL081 | YPL030W | 5 |
| DEL082 | YPL129W | 5 |
| DEL083 | YPR060C | 5 |

Example 2

Study of Detection Sensitivity of Homozygous Diploid Gene-Disrupted Strain Using Promoter Assay As described above, when a detectable sensitivity is low, generally, pre-treatment such as concentration of a sample and the like becomes necessary and, in particular, when concentration is performed at a high rate, there is a possibility that a chemical as a subject is lost during a concentration procedure. A detection sensitivity of a chemical by a reporter·gene·assay method depends on sensitivity of an index organism. As a method of increasing sensitivity without changing an index organism, it is contemplated that a line having high sensitivity is selected among the same species. It is thought that, there is a possibility that sensitivity is improved due to various reasons by lost of a gene, such as increase in membrane permeability of a chemical due to lost of a gene of a constitutional component of a cell membrane, and response to a chemical at a low concentration due to lost of a gene involved in detoxification mechanism and, herein, as a line exhibiting a different nature, an attention is paid to a gene-disrupted strain. How a chemical damages an organism, and how an organism responses thereto has not previously been analyzed comprehensively. Then, by selecting a gene-disrupted strain exhibiting sensitivity to many kinds of chemicals by experiment, the gene-disrupted strain may be used as an index organism. There are about 6000 genes in a yeast cell, and since strains with a deleted gene have already been made and sold regarding almost all genes, screening was performed using them.

Method

1) Selection of Gene-Disrupted Strain

In a gene-disrupted strain, a growing rate becomes small so much, or medium components in which the strain can be grown are different in some cases, depending on a disrupted gene. Then, in the present experiment studying a host cell of a promoter assay method, in view of easy comparison with a control experiment, among gene-disrupted strains obtained as the result of Example 1, a few strains which have sensitivity to many chemicals and are grown by the same procedure as that of a parent strain were selected. Selected gene-disrupted strains are 8 strains of DEL000, DEL002, DEL011, DEL014, DEL016, DEL019, DEL022 and DEL025 in Table 7. Further, as a control, a parent strain, BY4743 was used.

2) Preparation of Transformant

A competent cell of each of a parent strain of a gene-disrupted strain and selected gene-disrupted strains was prepared. This competent cell was transformed using two kinds of prepared plasmids for promoter assay, p-YBR072W (in which GFP was connected understream of a promoter of YBR072W) and p-YPL171C (in which GFP was connected downstream of a promoter of YPL171C). YPL171C is a gene encoding NAPDH dehydrogenase, YBR072W is a gene encoding a heat shock protein, and both of them exhibit response to a plurality of kinds of chemicals when prompter assay is performed.

Specifically, p-YBR072W was prepared by the following procedure. Primers for amplifying a polynucleotide (SCPD: disclosed in the Promoter Database of *Saccharomyces cerevisiae*) (SEQ ID No:1) containing a promoter sequence of a yeast gene YBR072W by PCT were prepared. Primers were designed using Oligo 4.0-S, Sequencher I, a McIntosh version, which is a software for designing primers, a nucleotide sequence of an upper primer is:

```
GCAGTCAACGAGGAGCGAATCAG,       (SEQ ID NO: 2)
``` and a nucleotide sequence of a lower primer is:

```
GTTAATTTGTTTAGTTTGTTTG         (SEQ ID NO: 3)
```

In PCR, as a template, a yeast chromosome (*Saccharomyces cerevisiae* S288C, Cat. 40802, Research Genetics, Inc.) was used and, as a reagent a commercially available kit (KOD DNA Polymerase; code KOD-101, Toyobo) was used.

As a vector, pYES2 (pYES2, Cat no: V825-20, Invitrogen Corporation, USA) (R. W. OLD, S. B. Primrose Principle of Gene Manipulation, Original Document, 5th Edition, Baifu-Kan Co., Ltd., pp. 234-263, 2000)) as a YEp-type shuttle vector which is replicated in both of *Escherichia coli* and yeast was used. As a polynucleotide encoding a marker protein, GFP, a part (SEQ ID NO: 4) of GFP of a vector pQBI 63 (Cat no. 54-0082, Wako Pure Chemical Industries Ltd.) was used. First, a vector in which a polynucleotide of GFP was inserted into a multiple cloning site of pYES2 was made. Then, a part of a GAL promoter pYES2 was replaced with a polynucleotide containing a promoter sequence of YBR072W which is a yeast gene, to obtain an objective plasmid vector. A procedure of insertion of a polynucleotide containing GFP and a promoter sequence was performed by selecting appropriate restriction enzymes.

Then, yeast *Saccharomyces cerevisiae* BY4743 (YKO Plate sets: Yeast Deletion Homozygous Diploid complete set, ResGen™, Invitrogen) was transformed with this plasmid vector. A procedure of transformation is shown below.

1) A yeast cell, *Saccharomyces cerevisiae* BY4743 is shaking-cultured on 200 mL of a YPD medium until OD660 becomes 0.5.

2) Cells are collected and suspended in 5 mL of a TE-buffer 3) 250 µL of 2.5 M lithium acetate is added.

4) Each 300 μL is dispended, and 10 μL of the plasmid vector is added, followed by culturing at 30° C. for 30 minutes.
5) 700 μL of 50% PEG4000 is added, followed by shaking-culturing at 30° C. for 60 minutes.
6) After heat shock (42° C., 5 minutes), the culture is rapidly cooled.
7) The culture is washed with 1 M sorbitol twice.
8) This is seeded on an agar plate made of a minimum nutrient medium (obtained by adding a necessary amino acid (histidine, leucine) to a SD medium).

Transformation was confirmed on a selective medium (SD medium (Yeast nitrogen base without amino acids (Difco 0919-15)+glucose+amino acid (histidine, leucine). For colonies which were grown an agar plate of the selective medium were further confirmed for amino acid auxotrophy.

And, p-YPL171C was prepared as follows:

Primers for amplifying a polynucleotide (SCPD: disclosed in The Promoter Database of *Saccharomyces cerevisiae*) (SEQ ID No. 5) containing a promoter sequence of a yeast gene YPL171C by PCR was prepared. Primers were designed using Oligo 4.0-S, Sequencher I, a McIntosh version, which is a software for designing primers, a nucleotide sequence of an upper primer is:

ACGCCCCTTCCTTTTTCCCTTTC        (SEQ ID No: 6)

and a nucleotide sequence of a lower primer is:

CTTCTAAATTTAAACTTCGCTA         (SEQ ID No: 7)

In PCR, as a template, a yeast chromosome (*Saccharomyces cerevisiae* S288C, Cat. 40802, Research Genetics, Inc.) was used and, as a reagent, a commercially available kit (KOD DNA Polymerase; code KOD-101, Toyobo) was used.

As a vector, pYES2 (pYES2, Cat no: V825-20, Invitrogen Corporation, USA) (R. W. Old, S. B. Primrose, Principle of Gene Manipulation, original document 5th edition, Baifukan Co., Ltd., pp. 234-263, 2000) as a YEp-type shuttle vector which is replicated in both of *Escherichia coli* and yeast was used. In addition, as a polynucleotide encoding a marker protein GFP, a part (SEQ ID No: 4) of GFP of a vector pQBI 63 (Cat no. 54-0082, Wako Pure Chemical Industries Ltd.) was used. First, a vector in which a polynucleotide of GFP was inserted into a multiple cloning site of pYES2 was prepared. Then, a part of a GALL promoter of pYES2 was replaced with a polynucleotide containing a prompter sequence of YPL171C which is a yeast gene, to obtain an objective plasmid vector. A procedure for inserting a polynucleotide containing GFP and a promoter sequence was performed by selecting appropriate restriction enzymes.

Then, a yeast *Saccharomyces cerevisiae* BY4743 (YKO Plate sets: Yeast Deletion Homozygous Diploid complete set, ResGen™, Invitrogen) was transformed with this plasmid vector. A procedure of transformation is shown below.

1) A yeast cell, *Saccharomyces cerevisiae* BY4743 is shaking-cultured on 200 mL of a YPD medium until OD660 becomes 0.5.
2) Cells are collected and suspended in 5 mL of a TE-buffer
3) 250 μL of 2.5 M lithium acetate is added.
4) Each 300 μL is dispended, and 10 μL of the plasmid vector is added, followed by culturing at 30° C. for 30 minutes.
5) 700 μL of 50% PEG4000 is added, followed by shaking-culturing at 30° C. for 60 minutes.
6) After heat shock (42° C., 5 minutes), the culture is rapidly cooled.
7) The culture is washed with 1 M sorbitol twice.
8) This is seeded on an agar plate made of a minimum nutrient medium (obtained by adding a necessary amino acid (histidine, leucine) to a SD medium).

Transformation was confirmed on a selective medium (SD medium (Yeast nitrogen base without amino acids (Difco 0919-15)+glucose+amino acid (histidine, leucine). For colonies which were grown an agar plate of the selective medium were further confirmed for amino acid auxotrophy.

3) Chemical Sensitivity Test

The resulting transformant was grown to the steady state by shaking-culturing on a SD medium (histidine, leucine) at 25° C. The transformant in the steady state was diluted 500-fold with the same medium, shaking-cultured at 25° C. for 15 hours and, after it was confirmed that an absorbance at 600 nm was 0.2 to 0.5 as a logarithmic growth phase, chemicals having different concentrations were loaded. After loading of chemicals, fluorescence of cells which had been cultured for 4 hours was measured using a flow cytometer (FITC filter, EPICS XL-MCL, Bechmancoulter), and this was adopted as an expression amount of GFP (green fluorescence protein) which is a marker gene. A fluorescence intensity of 10000 cells was measured with a flow cytometer by one measurement and an average of fluorescence intensities of all cells was obtained, and was adopted as a measured value. Similarly, a fluorescence intensity of a cell to which a chemical had not been loaded was obtained, and results are shown as a fluorescence intensity ratio.

4) Results

A detection sensitivity of a promoter assay method when gene-disrupted strains DEL000, DEL002, DEL011, DEL014, DEL016, DEL019, DEL022, and DEL025 (Table 7) were used as a host cell, was studied. As a chemical to be loaded, sodium metaarsenite, cadmium chloride, benthiocarb and mercury (II) chloride which exhibit response when BY4743 was a host, were selected and used. A dilution series of a chemical was made, a loading test was performed and results are shown in FIGS. 1 to 5.

FIG. 1 shows that a gene-disrupted strain DEL011 responded to sodium metaarsenite at a concentration which is 1/3 a concentration of a parent strain.

Figure 2:
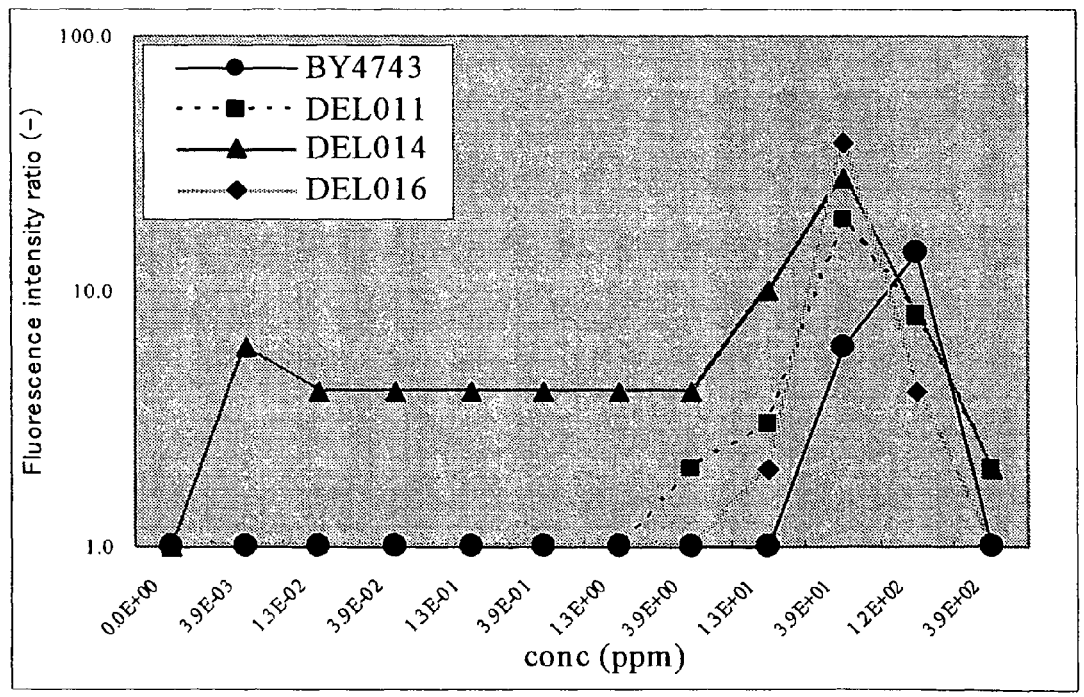
FIG. 2 is a graph showing a sensitivity to sodium metaarsenite in gene-disrupted stains DEL011, DEL014 and DEL016 transformed with a plasmid p-YBR072W.

FIG. 2 shows that a gene-disrupted strain DEL011 responded to sodium metaarsenite at a concentration which is 1/10 a concentration of a parent strain, a gene-disrupted strain DEL014 at a concentration which is 1/3000 a concentration of a parent strain, and a gene-disrupted strain DEL016 at a concentration which is 1/3 a concentration of a parent strain.

Figure 3:
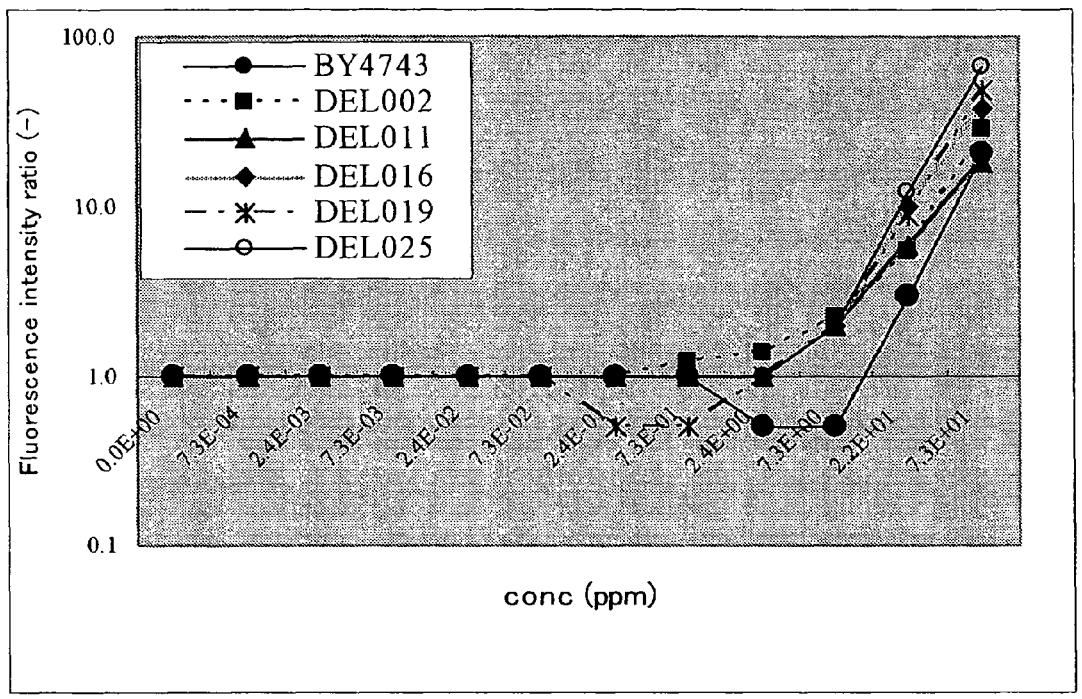
FIG. 3 is a graph showing a sensitivity to cadmium chloride in gene-disrupted strains DEL002, DEL010, DEL016, DEL019 and DEL025 transformed with a plasmid p-YBR072W.

FIG. 3 shows that a gene-disrupted strain DEL002 responded to cadmium chloride at a concentration which is 1/3 a concentration of a parent strain, a gene-disrupted strain DEL011 at a concentration which is 1/3 a concentration of a parent strain, DEL016 at a concentration which is 1/3, DEL019025 at a concentration which is 1/3, and a gene-disrupted strain DEL at a concentration which is 1/3 a concentration of a parent strain.

Figure 4:
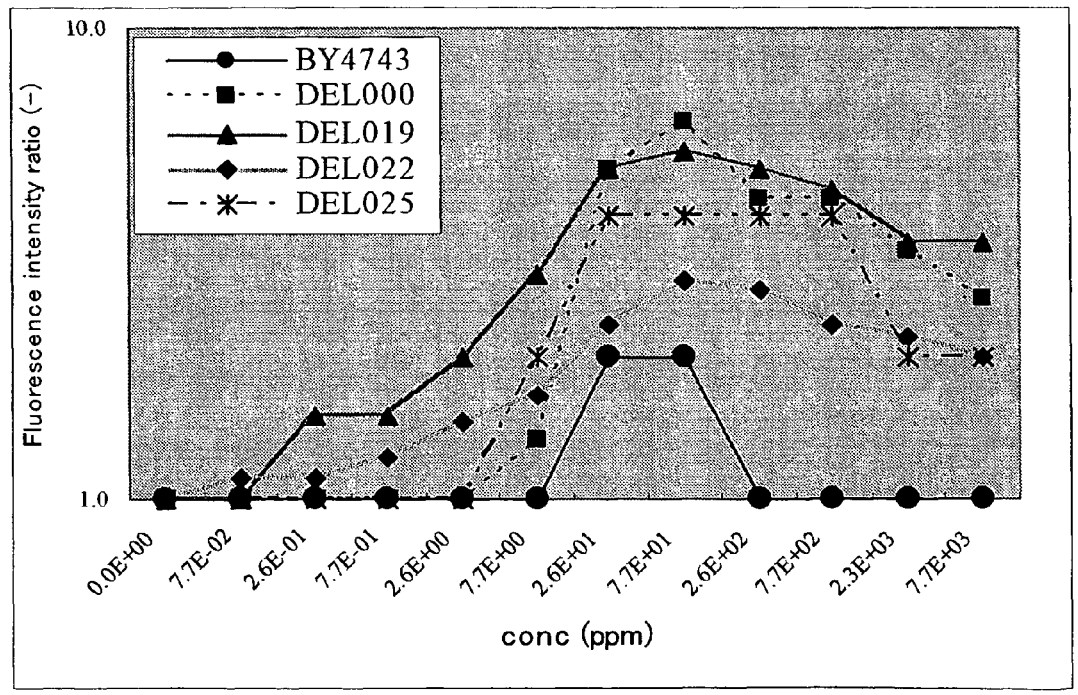
FIG. 4 is a graph showing a sensitivity to bentiocarb in gene-disrupted strains DEL000, DEL019, DEL022 and DEL025 transformed with a plasmid p-YBR072W.

FIG. 4 shows that a gene-disrupted strain DEL000 responded to benthiocarb at a concentration which is 1/3 a concentration of a parent strain, a gene-disrupted strain DEL 019 at a concentration which is 1/100 a concentration of a parent strain, DEL022 at a concentration which is 1/10, and a gene-disrupted strain DEL025 at a concentration which is 1/3.

Figure 5:
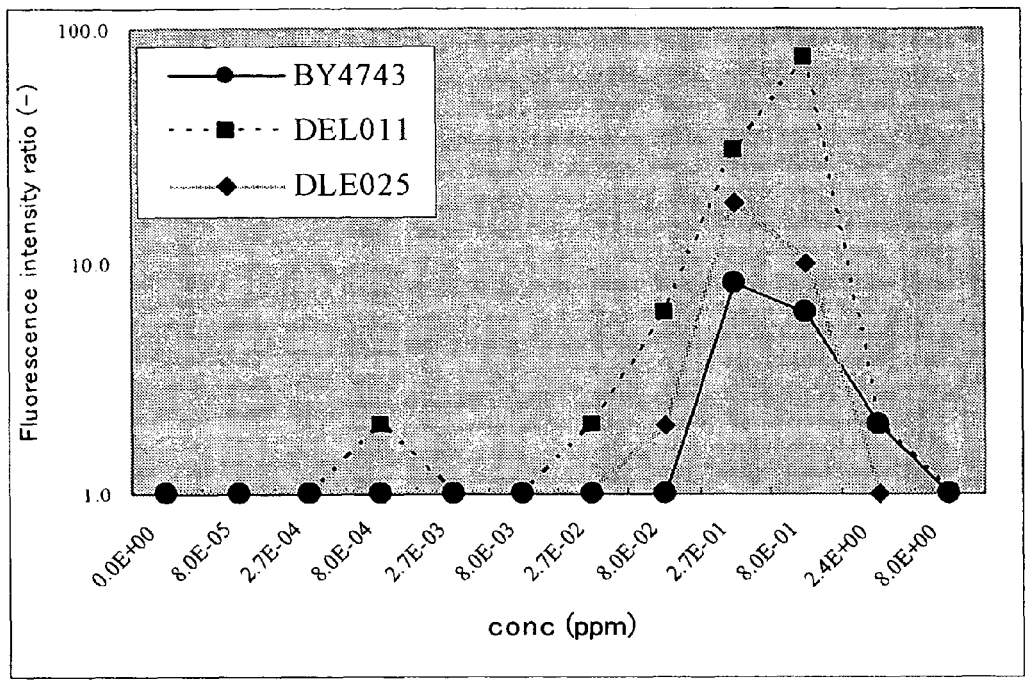
FIG. 5 is a graph showing a sensitivity to mercuric chloride in gene-disrupted strains DEL011, DEL016 and DEL025 transformed with a plasmid p-YPL171C.

FIG. 5 shows that a gene-disrupted strain DEL011 responded to mercuric chloride at a concentration which is 1/10 a concentration of a parent strain, and a gene-disrupted strain DEL016 at a concentration which is 1/3.

Like this, it was confirmed that DEL000, DEL002, DEL011, DEL014, DEL016, DEL019, DEL022 and DEL025 have responsiveness to a chemical which is 3-fold to 100-fold higher than that of a parent strain, BY4743. Particularly, even at a concentration which is 1/1000 a detectable concentration of a parent strain, a significant difference was seen in DEL0014, as compared with BY4743 (FIG. 2).

Example 3

Study of Detection Sensitivity of Homozygous and Heterozygous Diploid Gene-Disrupted Strains Using Promoter Assay Method
1) Preparation of Gene-Disrupted Strain
a-1) Preparation of Gene-Disrupted Strain Transformation Cassette In order to prepare a gene-disrupted strain transformation cassette, genes having chemical sensitivity; YPR036W (DEL000), YDL151C(DEL001), YGL026C(DEL003), YHR039C-A(DEL006), YKL080W(DEL007), YLR447C (DEL008), YGR006W(DEL012), YGR105W(DRL013), YJR104C(DEL014), YGL206C(DEL018), YIL036W (DEL019), YKL119C(DEL020), YLR226W(DEL022) and YLR311C(DEL025) in Table 7 were selected, and each gene was replaced with a transformation marker such as kanamycin resistance. As primers for performing PCT amplification, a N-terminal side (ORF(upper)) and a C-terminal side (ORF (lower)) in each ORF were used. A length of a sequence (ORF(upper) and ORF(lower)) of a primer homologues with ORF was 46 or 50 bp.

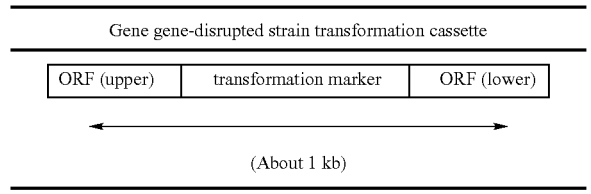

(About 1 kb)

Using these primers, and using a plasmid containing a gene sequence of a transformation marker as a template, a PCR reaction was performed, and electrophoresis was preformed and, as a result, about 1 KD uniform bands were confirmed in primers for all genes. These PCR products were used as a gene-disrupted strain transformation cassette.

a-2) Preparation and Transformation of Competent Cell

As a strain from which a yeast gene-disrupted strain was prepared, W303 a mating-type ATCC200903 (MATa made2-1 trp1-1 leu2-3 leu2-112 his3-11 his3-15 ura3-1 can1-100) and W303 α mating type ATCC201238 (MATα ade2-1 trp1-1 leu2-3 leu2-112 his3-11 his3-15 ura3-1 can1-100) were used.
W303 a mating-type and W303α mating type competent cells were prepared and transformed with the previously prepared gene-disrupted strain transformation cassettes. For preparing and transforming competent cells, a commercially available kit (S.c. easyComp™ Transformation Kit: Invitrogen) was used.

a-3) Confirmation of Transformation

Transformation was confirmed using PCR. An upper primer was set in a promoter region of a targeting gene and a lower primer was set in a transformation marker, and PCR was performed. As a result, when an ORF site is replaced with a transformation marker, and a gene is disrupted, a site between primers is amplified and, when a gene is not disrupted, the site is not amplified, thereby, transformation could be confirmed.

b) Preparation of Homozygous Diploid and Heterozygous Diploid

By mixing-culturing haploids of Saccharomyces crevisiae a and α mating-types, an a/α-type diploid can be prepared.

A W303 a mating type (ATCC200903) and a W303α mating type (ATCC201238) in which the same gene was gene disruption-manipulated were mated by a mating procedure (Yeast Gene Experimental Manual: Maruzen Co., Ltd., p 83-92) to prepare homozygous diploids. Separately, mating of a W303a mating type, and a non-gene-disrupted W303α type was performed by the similar procedure to prepare heterozygous diploids.

By such the procedure, homozygous diploids of DEL000, DEL001, DEL003, DEL006, DEL007, DEL008, DEL012, DEL013, DEL014, DEL018, DEL019, DEL020, DEL022 and DEL025 in Table 7 were prepared. In addition, heterozygous diploids in which DEL006, DEL014 and DEL 022 were mated with a non-gene-disrupted strain (hereafter, referred to as DEL006 heterozygous diploid, DEL 014 heterozygous diploid, DEL022 heterozygous diploid) and, further, a heterozygous diploid in which DEL000 and DEL014 were mated (hereafter, referred to as DEL000/014 heterozygous diploid) were prepared.

c) Preparation of Promoter Assay Transformant

Competent cells of W303 ATCC201239 (MATa/MATα leu2-3/leu2-3 leu2-112/leu2-112 trp1-1/trp1-1 ura3-1/ura3-1 his 3-11/his3-11 his3-15/his3-15 ade2-1/ade2-1 can1-100/can1-100) which is a parent strain of gene-disrupted strains, and each of prepared gene-disrupted strains were prepared. The competent cells were transformed using two kind of prepared plasmid for promoter assay, p-YBR072W (in which GFP is connected downstream of a promoter of YBR072W) and p-YPL171C (in which GFP is connected downstream of a promoter of YPL171C).

Specifically, p-YBR072W was prepared by the following procedure.

Primers for amplifying a polynucleotide (SCPD: disclosed in The Promoter Database of Saccharomyces cerevisiae) (SEQ ID No:1) containing a promoter sequence of a yeast gene of YBR072W by PCR were prepared. Primers were designed using Oligo 4.0-S, Sequencher I, a McIntosh version, which is a software for designing primers, a nucleotide sequence of an upper primer is:

GCAGTCAACGAGGAGCGAATCAG          (SEQ ID No: 2)

and a nucleotide sequence of a lower primer is:

GTTAATTTGTTTAGTTTGTTTG           (SEQ ID No: 3)

In PCR, as a template, a yeast chromosome (Saccharomyces cerevisiae S288C, Cat. 40802, Research Genetics, Inc.) was used and, as a reagent, a commercially available kit (KOD DNA Polymerase; code KOD-101, Toyobo) was used.

As a vector, pYES2 (pYES2, Cat no: V825-20, Invitrogen Corporation, USA)(R. W. OLD, S. B. Primrose Principle of Gene Manipulation, Original Document, 5th Edition, Baifukan Co., Ltd., pp. 234-263, 2000)) as a YEp-type shuttle vector which is replicated in both of Escherichia coli and yeast was used. As a polynucleotide encoding a marker protein, GFP, a part (SEQ ID NO: 4) of GFP of a vector pQBI 63 (Cat no. 54-0082, Wako Pure Chemical Industries Ltd.) was used. First, a vector in which a polynucleotide of GFP was inserted into a multiple cloning site of pYES2 was prepared. Then, a part of a GAL promoter of pYES2 was replaced with a polynucleotide containing a promoter sequence of YBR072W which is a yeast gene, to obtain an objective plasmid vector. A procedure of insertion of a polynucleotide containing GFP and a promoter sequence was performed by selecting appropriate restriction enzymes.

Then, a yeast strain or a gene-disrupted strain was transformed with this plasmid vector. A procedure of transformation is shown below.
1) A yeast cell, *Saccharomyces cerevisiae* W303, is shaking-cultured on 200 mL of a YPD medium until ODD660 becomes 0.5.
2) Cells are collected and suspended in 5 mL of a TE-buffer
3) 250 μL of 2.5 M lithium acetate is added.
4) Each 300 μL is dispended, and 10 μL of the plasmid vector is added, followed by culturing at 30° C. and 30 minutes.
5) 700 μL of 50% PEG4000 is added, followed by shaking culturing at 30° C. for 60 minutes.
6) After heat shock (42° C., 5 minutes), the culture is rapidly cooled.
7) The culture is washed with 1 M sorbitol twice.
8) This is seeded on an agar plate made of a minimum nutrient medium (obtained by adding a necessary amino acid (adenine, histidine, tryptophan, leucine) to a SD medium).

Transformation was confirmed on a selective medium (SD medium (Yeast nitrogen base without amino acids (Difco 0919-15)+glucose+amino acid (adenine, histidine, tryptophan, leucine). Colonies which were grown on an agar plate of the selective medium were further confirmed for amino acid auxotrophy.

And, p-YPL171C was prepared as follows:
Primers for amplifying a polynucleotide (SCPD: disclosed in The Promoter Database of *Saccharomyces cerevisiae*) (SEQ ID No. 5) containing a promoter sequence of a yeast gene YPL171C by PCR was prepared. Primers were designed using Oligo 4.0-S, Sequencher I, a McIntosh version, which is a software for designing primers, a nucleotide sequence of an upper primer is:

```
ACGCCCCTTCCTTTTTCCCTTTC          (SEQ ID No: 6)
``` and a nucleotide sequence of a lower primer is:

```
CTTCTAAATTTAAACTTCGCTA           (SEQ ID No: 7)
```

In PCR, as a template, a yeast chromosome (*Saccharomyces cerevisiae* S288C, Cat. 40802, Research Genetics, Inc.) was used and, as a reagent, a commercially available kit (KOD DNA Polymerase; code KOD-101, Toyobo) was used.

As a vector, pYES2 (pYES2, Cat no: V825-20, Invitrogen Corporation, USA) (R. W. Old, S. B. Primrose, Principle of Gene Manipulation, original document 5th edition, Baifukan Co., Ltd., pp. 234-263, 2000) as a YEp-type shuttle vector which is replicated in both of *Escherichia coli* and yeast was used. In addition, as a polynucleotide encoding a marker protein GFP, a part (SEQ ID No: 4) of GFP of a vector pQBI 63 (Cat no. 54-0082, Wako Pure Chemical Industries Ltd.) was used. First, a vector in which a polynucleotide of GFP was inserted into a multiple cloning site of pYES2 was prepared. Then, a part of a GAL1 promoter of pYES2 was replaced with a polynucleotide containing a prompter sequence of YPL171C which is a yeast gene, to obtain an objective plasmid vector. A procedure for inserting a polynucleotide containing GFP and a promoter sequence was performed by selecting appropriate restriction enzymes.

Then, a parent strain and a gene-disrupted strain were transformed with this plasmid vector. A procedure of transformation is shown below.
1) A yeast cell, *Saccharomyces cerevisiae* BY4743 is shaking-cultured on 200 mL of a YPD medium until OD660 becomes 0.5.
2) Cells are collected and suspended in 5 mL of a TE-buffer
3) 250 μL of 2.5 M lithium acetate is added.
4) Each 300 μL is dispended, and 10 μL of the plasmid vector is added, followed by culturing at 30° C. for 30 minutes.
5) 700 μL of 50% PEG4000 is added, followed by shaking-culturing at 30° C. for 60 minutes.
6) After heat shock (42° C., 5 minutes), the culture is rapidly cooled.
7) The culture is washed with 1 M sorbitol twice.
8) This is seeded on an agar plate made of a minimum nutrient medium (obtained by adding a necessary amino acid (histidine, leucine) to a SD medium).
3) Chemical Sensitivity Test The resulting transformant was grown to the steady state by shaking-culturing on a SD medium (adenine, hystidine, triptophan, leucine) at 25° C. The transformant in the steady state was diluted 500-fold with the same medium, shaking-cultured at 25° C. for 15 hours and, after it was confirmed that an absorbance at 600 nm was 0.2 to 0.5 as a logarithmic growth phase, chemicals having different concentrations were loaded. After loading of chemicals, fluorescence of cells which had been cultured for 4 hours was measured using a flow cytometer (FITC filter, EPICS XL-MCL, Bechman-coulter), and this was adopted as an expression amount of GFP (green fluorescence protein) which is a marker gene. A fluorescence intensity of 10000 cells was measured with a flow cytometer by one measurement and an average of fluorescence intensities of all cells was obtained, and was adopted as a measured value. Similarly, a fluorescence intensity of a cell to which a chemical had not been loaded was obtained, and results are shown as difference in a fluorescence intensity.

Results

Detection sensitivity of a promoter assay method when homozygous diploids of gene-disrupted strains DEL000, DEL001, DEL003, DEL006, DEL007, DEL008, DEL012, DEL013, DEL014, DEL018, DEL019, DEL020, DEL022 and DEL025 (Table 7) were used as a host cell was studied. Further, a detection sensitivity of a promoter assay method when heterozygous diploids of DEL006, DEL014 and DEL022 and a non-gene-disrupted strain, or a heterozygous diploid of DEL000 and DEL014 were used as a host cell, was studied. As a chemical to be loaded, sodium metaarsenite and thiuram exhibiting response when W303 was used as a host were selected and used in a promoter assay method using a plasmid p-YPL171C and benthiocarb was selected and used for p-YER072W. A dilution series of a chemical was prepared and a loading test was performed. Results are shown in FIG. 6 to FIG. 11

Figure 6:
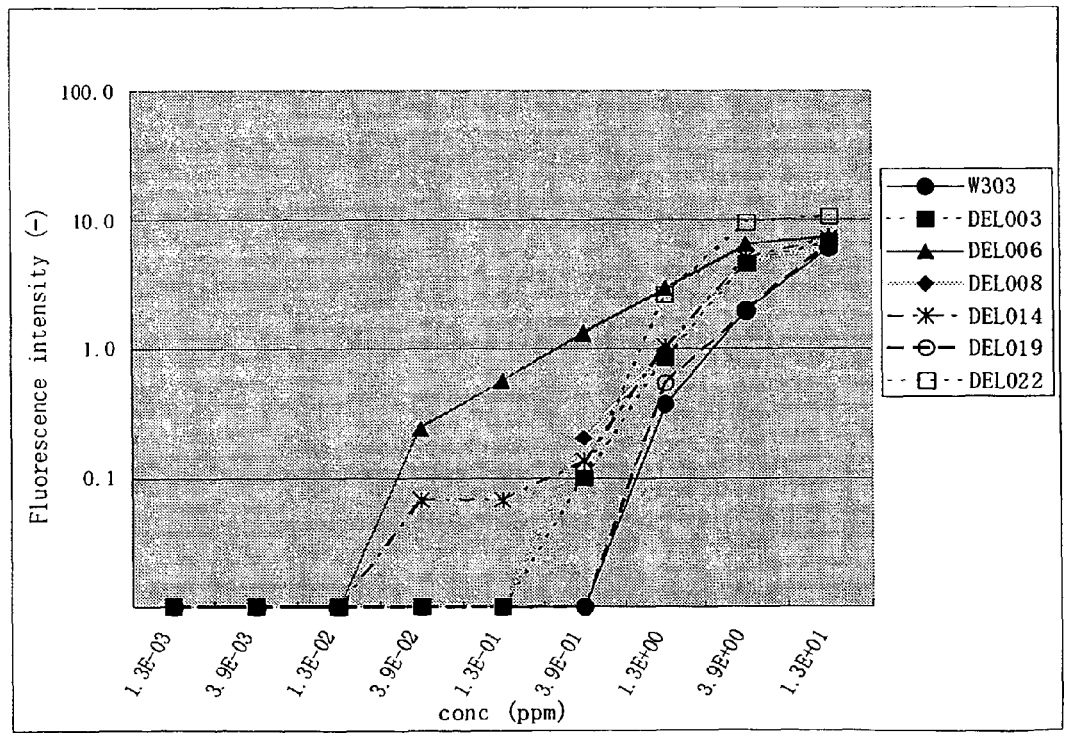
FIG. 6 is a graph showing a sensitivity to sodium metaarsenite in gene-disrupted strains DEL006 and DEL014 transformed with a plasmid p-YPL171C at a concentration which is 1/30 a concentration of a gene-non-disrupted strain, and in DEL003, DEL008 and DEL022 at a concentration which is 1/3 a concentration of a gene-non-disrupted strain. All of gene-disrupted strains are a homozygous diploid.

FIG. 6: DEL003, DEL006, DEL008, DEL014, DEL019 and DEL022 exhibited a fluorescent intensity equivalent to or more than that of a non-gene-disrupted stain by loading of a chemical at the same concentration. All gene-disrupted strains are a homozygous diploid.

Figure 7:
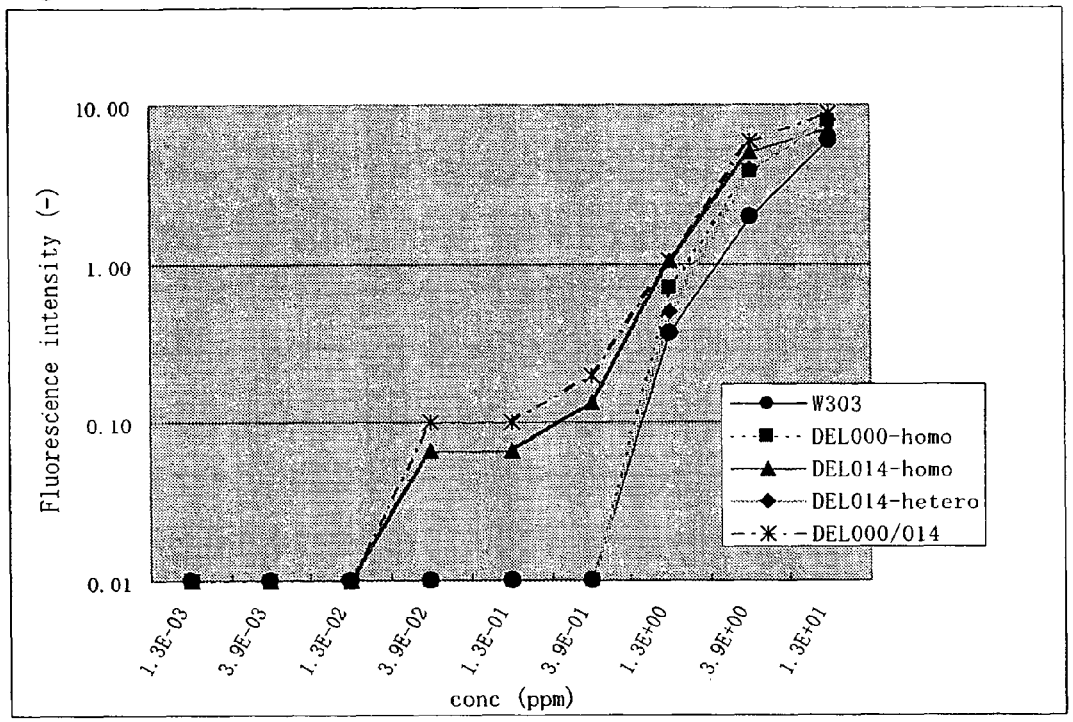
FIG. 7 is a graph showing a sensitivity to sodium metaarsenite in a homozygous diploid of a gene-disrupted stain DEL014 transformed with a plasmid p-YPL171C, and in a heterozygous diploid DEL000/014 at a concentration which is 1/30 a concentration of a gene-non-disrupted strain.

FIG. 7: A DEL000 homozygous diploid, a DEL014 heterozygous diploid, a DEL 014 homozygous diploid and a DEL 000/014 heterozygous diploid exhibited a fluorescent intensity equivalent to or more than that of a non-gene-disrupted strain by loading of a chemical at the same concentration.

Figure 8:
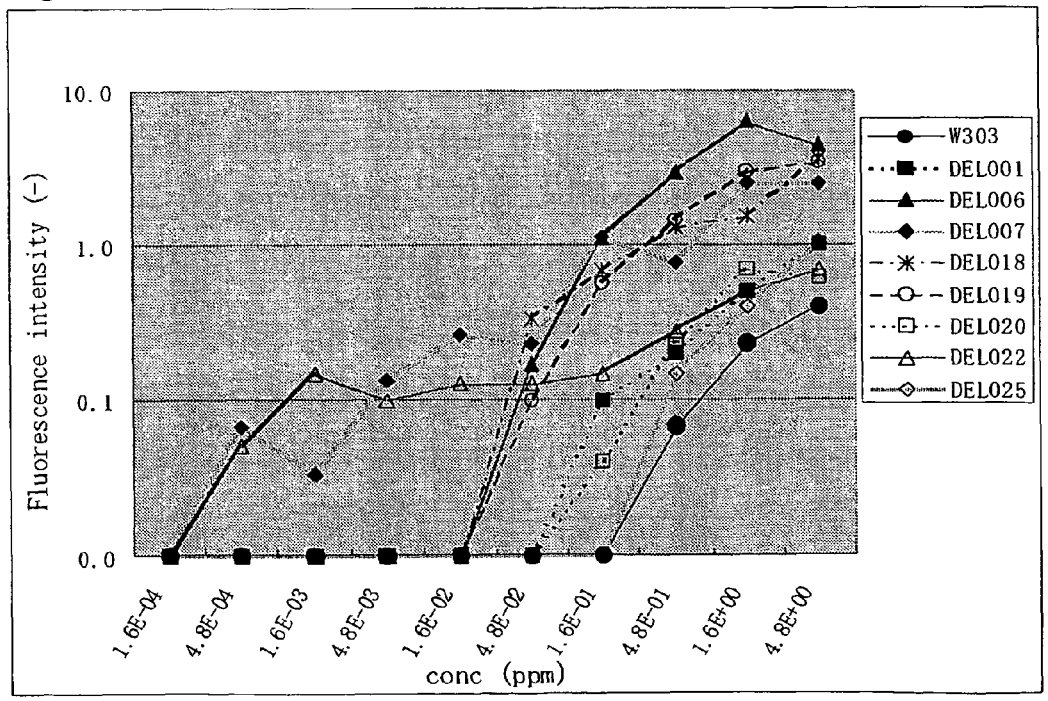
FIG. 8 is a graph showing a sensitivity to thiuram in gene-disrupted stains DEL007 and DEL022 transformed with a plasmid p-YPL171C at a concentration which is 1/1000 a concentration of a gene-non-disrupted strain, and in DEL001 and DEL0020 at a concentration which is 1/3 a concentration of a gene-non-disrupted stain. All of gene-disrupted strains are a homozygous diploid.

FIG. 8: DEL001, DEL006, DEL007, DEL018, DEL019, DEL020, DEL022 DEL025 exhibited a fluorescent intensity equivalent to or more than that of a non-gene-disrupted strain by loading a chemical at the same concentration. All gene-disrupted strains are a homozygous diploid.

Figure 9:
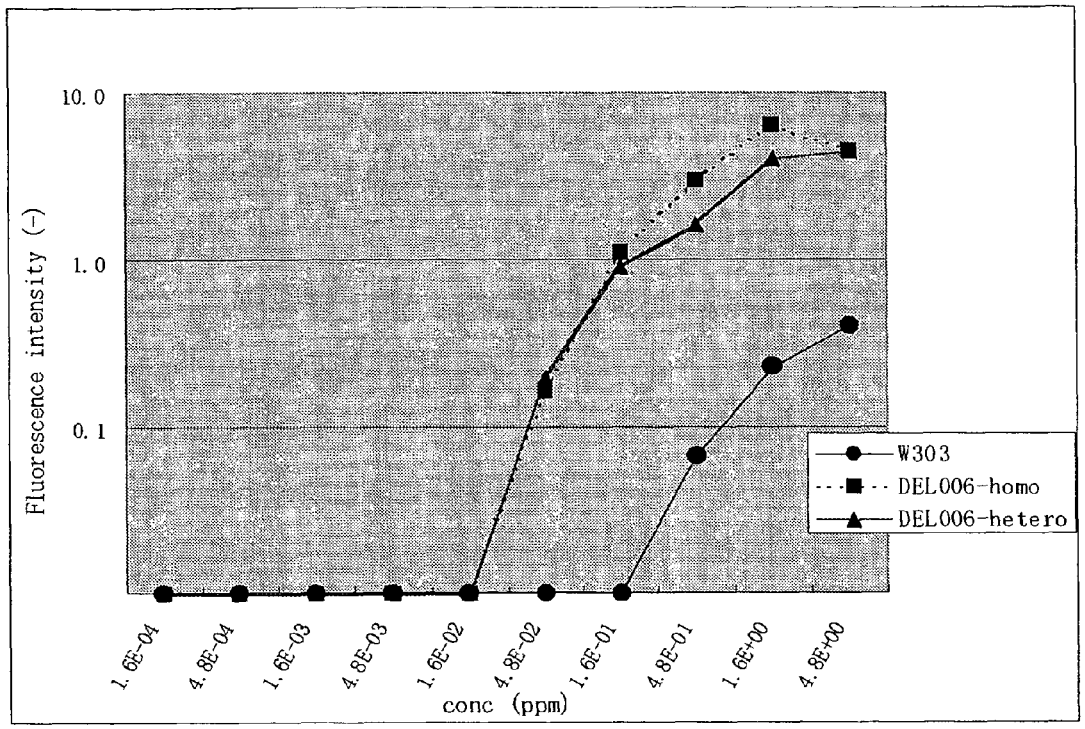
FIG. 9 is a graph showing a sensitivity to thiuram in a homozygous diploid and a heterozygous diploid of a gene-disrupted strain DEL006 transformed with a plasmid p-YPL171C at a concentration which is 1/10 a concentration of a gene-non-disrupted strain.

FIG. 9: A fluorescent intensity equivalent to or more than that of a non-gene-disrupted strain was exhibited by loading of a chemical at the same concentration.

Figure 10:
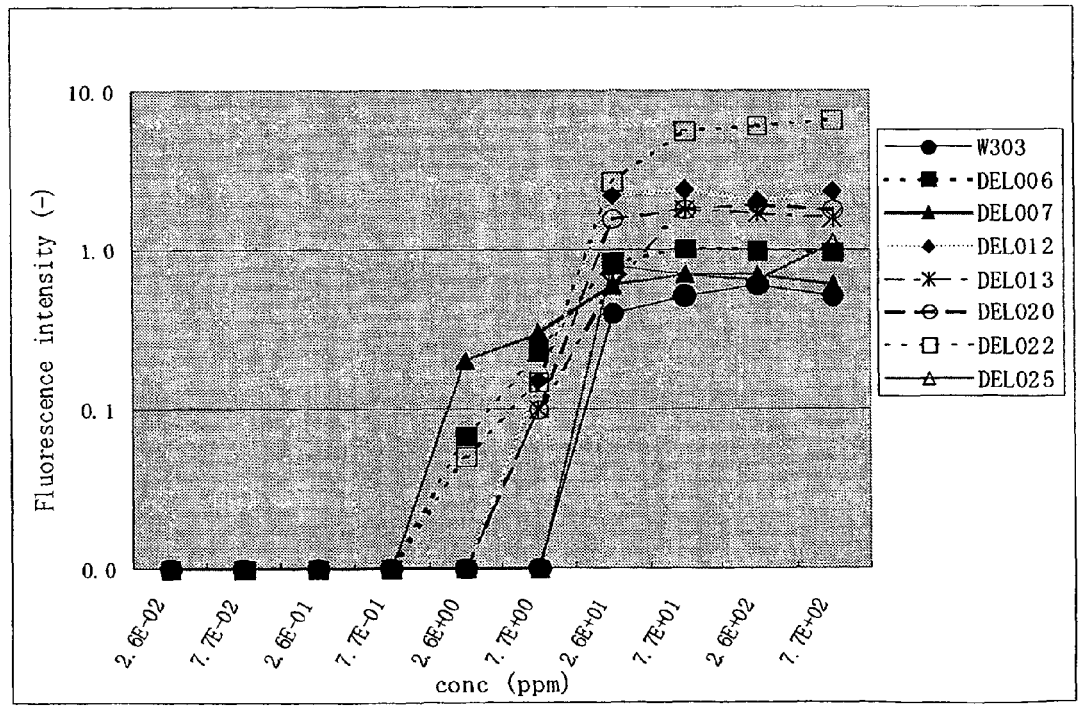
FIG. 10 is a graph showing a sensitivity to bentiocarb in gene-disrupted strains DEL006, EL007 and DEL022 transformed with a plasmid p-YBR072W at a concentration which is 1/10 a concentration of a gene-non-disrupted strain, and in DEL012, DEL013 and DEL020 at a concentration which is 1/3 a concentration of a gene-non-disrupted strain. All of gene-disrupted strains are a homozygous diploid.

FIG. 10: DEL006, DEL007, DEL012, DEL013, DEL020, DEL022 and DEL025 exhibited a fluorescent intensity equivalent to or more than that of a non-gene-disrupted strain by loading of a chemical at the same concentration. All gene-disrupted strains are a homozygous diploid.

Figure 11:
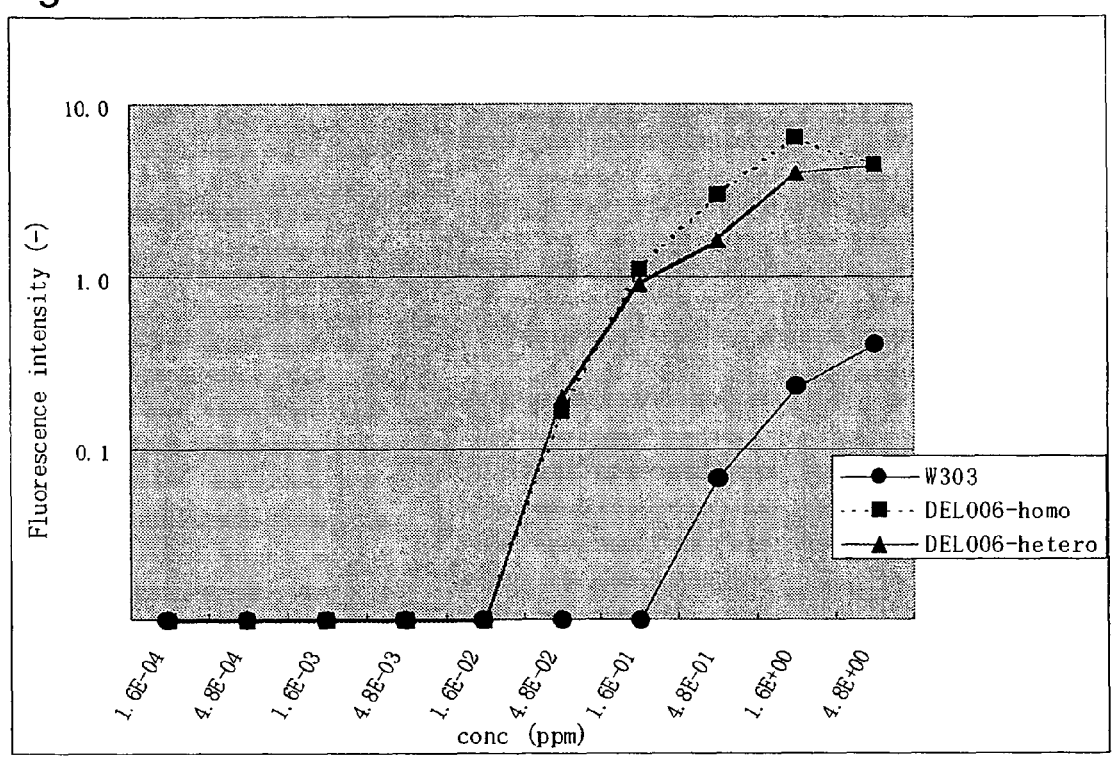
FIG. 11 is a graph showing a sensitivity to bentiocarb in a homozygous diploid of a gene-disrupted strain DEL0022 transformed with a plasmid p-YBR072W at a concentration which is 1/10 a concentration of a gene-non-disrupted strain, and in a heterozygous diploid of a gene-disrupted strain DEL0022 at a concentration which is 1/3 a concentration of a gene-non-disrupted strain.

FIG. 11: A fluorescent intensity more than that of a non-gene-disrupted strain was exhibited by loading of a chemical at the same concentration.

INDUSTRIAL APPLICABILITY

From the results of a chemical sensitivity test with a chemical plate, gene-disrupted strains were selected and, actually, by using them as a host cell, chemical-responding gene recombinant cells were prepared, and chemical responsiveness was measured. As a result, about 1000-fold sensitivity was obtained in some chemicals. From this, it was confirmed that a host cell having necessary sensitivity for practical field may be developed by using this procedure.

In this time study of a host cell, gene-disrupted strains exhibiting sensitivity to general chemicals were used, but possession of sensitivity to particular chemicals is considered to be advantageous in some cases, depending on a gene used in a reporter gene assay method and a targeting chemical.

What is claimed is:

1. A method of assaying whether a chemical is present in a test specimen or not, comprising
   culturing a first sample of a gene-disrupted strain of a yeast in the presence of the test specimen,
   culturing a second sample of the gene-disrupted strain of the yeast in the absence of the test specimen; and
   comparing cell response of the first sample with cell response of the second sample such that predetermined differences in cell response between the first sample and the second sample confirms presence of the chemical in the test specimen,
   wherein
   the disrupted gene is classified into:
   unclassified YBL056W; and/or
   an unclassified protein selected from the group: YDR149C, YLR285W, YLR311C, YOR331C, YPR123C, YDR525W-A, YDR539W, YDR540C, YGL246C, YJL204C, YLR282C, YLR287C, YLR290C, YJL188C, YJL192C, YJL211C, YKL037W, YLR283W, YLR312C, YLR315W, YLR320 W or YPL030W.

2. The method according to claim 1, wherein the cell response of a gene-disrupted strain to the chemical is life or death of a cell, and/or proliferation ability, a consumed amount of oxygen, enzyme activity and/or a change in gene expression.

3. The method according to claim 2, wherein the change in gene expression is a change in a RNA amount or a mRNA amount.

4. The method according to claim 2, wherein the change in gene expression is measured by reporter gene assay.

5. A method of assaying whether a chemical is present in a test specimen or not, comprising
   culturing a first sample of a gene-disrupted strain of a yeast in the presence of the test specimen,
   culturing a second sample of the gene-disrupted strain of the yeast in the absence of the test specimen; and
   comparing cell response of the first sample with cell response of the second sample such that predetermined differences in cell response between the first sample and the second sample confirms presence of the chemical in the test specimen, wherein the disrupted gene is classified into an unclassified protein, and the unclassified protein gene to be disrupted is YDR149C, YLR285W, YLR311C, YOR331C, YPR123C, YDR525W-A, YDR539W, YDR540C, YGL246C, Y3L204C, YLR282C, YLR287C, YLR290C, YJL188C, YJL192C, YJL211C, YKL037W, YLR283W, YLR312C, YLR315W, YLR320 W or YPL030W.

6. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is involved in a vacuole which is YKL080W, YLR447C, YHR060W, YPRO36W, YHR039C-A or YHR026W.

7. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into amino acid metabolism, nitrogen and sulfur metabolism, nucleotide metabolism, phosphate metabolism, C-compound and carbohydrate metabolism, lipid, fatty acid and isoprenoid metabolism, metabolism of vitamins, cofactors and prosthetic groups of metabolism and the metabolism gene to be disrupted is YGL026C, YGR180C, YDR127W, YCR028C, YLR284C, YOR221C, YAL021C, YGL224C, YBL042C, YDR148C, YHL025W, YLR307W, YLR345W, YLR354C, YPL129W, or YPR060C.

8. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into DNA processing, cell cycle of cell cycle and DNA processing, and the cell cycle and DNA processing gene to be disrupted is YGR180C, YDR150 W, YGL240W, YBL058W, YIL036W, YLR226W, YLR381W, YOR026W, YPL018W, YBL063W, YDR363W-A, YIR026C, YLR234W, YMR032W or YPL129W.

9. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into mRNA transcription, RNA transport of transcription, and the transcription gene to be disrupted is YGR006W, YIL036W, YKR082W, YLR226W, YML112W, YMR021C, YAL021C, YDR195W, YOL068C, YBR279W, YGL070C, YGL071W, YGL222C, YHL025W, YLR266C or YPL129W.

10. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into ribosome biosynthesis and translation control of protein synthesis, and the protein synthesis gene to be disrupted is YBL058W, YLR287C-A, YGRO84C or YLR344W.

11. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into protein targeting, sorting, translocation, protein modification, assembly of protein complex, proteolysis of protein fate, and the protein fate gene to be disrupted is YKL080 W, YLR447C, YGL240W, YGR105W, YKL119C, YDR414C, YHR060W, YLR292C, YGL227W or YGR270W.

12. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into nuclear transport, vesicular transport (Golgi network etc), vacuolar transport, cellular import, cytoskeleton-dependent transport and other intracellular transport activities of intracellular transport and transport mechanism, and the intracellular transport and transport mechanism gene to be disrupted is YPR036W, YDR027C, YHR039C, YKL080W, YLR447C, YKR082W, YLR292C or YBL063W.

13. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into stress response, detoxification of cell rescue, defense and pathogemicity, and the detoxification gene to be disrupted is YJR104C or YMR021C.

14. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into ionic homeostasis, cell sensitivity and response of intracellular environmental regulation/interaction, and the intracellular environmental regulation/interaction gene to be disrupted is YPR036W, YHR039C-B, YKL080W, YLR447C, YGL071W or YIR026C.

15. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into cell growth/morphogenesis, cell differentiation of cell fate, and the cell fate gene to be disrupted is YDL151C, YBL058W, YKR082W, YOL068C, YDR363W-A, YHL025W, YIR026C, YLR307W, YMR032W or YPL129W.

16. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into cell wall, cytoskeleton, nucleus, mitochondria of cell tissue control, and the cell tissue control gene to be disrupted is YDR027C, YDR414C, YLR381W, YGR084C or YMR032W.

17. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen, wherein
the disrupted gene is classified into ion transporter, vitamin/cofactor transporter, transport mechanism, other transport promotion of transport promotion, and the transport promotion gene to be disrupted is YPR036W, YHR026W, YHR039C, YKL080 W, YLR447C, YCR028C or YLR292C.

18. A method of assaying whether a chemical is present in a test specimen or not, comprising
culturing a first sample of a gene-disrupted strain of a yeast in the presence of the test specimen,
culturing a second sample of the gene-disrupted strain of the yeast in the absence of the test specimen; and
comparing cell response of the first sample with cell response of the second sample such that predetermined differences in cell response between the first sample and the second sample confirms presence of the chemical in the test specimen,
wherein
the disrupted gene is classified into unclassified, and the unclassified gene to be disrupted is YBL056W.

19. Use of a gene-disrupted strain of a yeast for assaying whether a chemical is present in a test specimen or not by culturing a gene-disrupted strain of the yeast in the presence of the test specimen, and using cell response of the gene-disrupted strain in accordance with the methodology set forth in any one of claims 2 to 4 and 1 and 5.

* * * * *

```
                            SEQUENCE LISTING

<160> NUMBER OF SEQ ID NOS: 7

<210> SEQ ID NO 1
<211> LENGTH: 1287
<212> TYPE: DNA
<213> ORGANISM: Saccharomyces cerevisiae

<400> SEQUENCE: 1
gcagtcaacg aggagcgaat cagacgccag tctttcctcc accaagagct cgatctcttc      60
catattttcc caagataatg actattccat tcacgatttg ttgtacgaag atattgaaga     120
gatggataaa acagacgctt tcaaaattaa caacacaata gcaatcgatg attctaaagc     180
tctctttgtc ttctgttcaa acgactcctc ctcaaggaca gcgtctatcg aaacattgca     240
cgaatcaaat ttggacaacc tggatatggg ttccagtaga aggacatcgt tggactttt      300 ttaatataac ctaccatagg acacactttg ttgttgatgt tggacaattc gttaattaag     360
agtccctaaa cggctctact agttccaacc tcactttgtt ttttcatttt tttatgtttt     420
ttctagaacc ttctttacgt gattctcgct cggaatccgt caatagaatg ttttcagtct     480
ccgtttcaat attctgcgca catcaatcat tttcttacta catacactaa cattactcct     540
agtttaattt aattgaattt ttaactttct tttctttca tttggcaatt tggctccttg     600
aaaacaagac tatgggtctc tctcataagc ctcagggggg gaccccaaaa aaataacgcg     660
gccatcttgc atgcaccgtt gaacctgtag cttacagtaa gccacaattc tcttaccttc     720
ttggcaatgt ggcacaaaat aatctggtta tgtgtcttca tttggtaatc actgggatgt     780
tactggggca gcagcaactc cgtgtgtacc cctaactccg tgtgtacccc taaagaacct     840
tgcctgtcaa ggtgcattgt tggatcggaa tagtaaccgt ctttacatga acatccacaa     900
ccaacgaaag tgcttttca agcattgctt gatttctaga aagatcgatg gttattccct     960
cccccttatg cgtccaaaaa tatagggtgc tcgtaacagt aaggtattcg cacttagcgt    1020
gctcgcaaca caaattaag taatatgcga gttttagatg tccttgcgga tctatgcacg     1080
ttcttgagtg gtatttcata acaacggttc tttttcaccc ttattcctaa acatataaat    1140
aggacctcca ttagttagag atctgttttt aatccattca cctttcattc tactctctta    1200
tactaataaa accaccgata aagatatatc agatctctat taaaacaggt atccaaaaaa    1260
gcaaacaaac aaactaaaca aattaac                                        1287

<210> SEQ ID NO 2
<211> LENGTH: 23
<212> TYPE: DNA
<213> ORGANISM: Artificial Sequence
```

```
<220> FEATURE:
<223> OTHER INFORMATION: Synthesized

<400> SEQUENCE: 2
gcagtcaacg aggagcgaat cag                                              23

<210> SEQ ID NO 3
<211> LENGTH: 22
<212> TYPE: DNA
<213> ORGANISM: Artificial Sequence
<220> FEATURE:
<223> OTHER INFORMATION: Synthesized

<400> SEQUENCE: 3
gttaatttgt ttagtttgtt tg                                               22

<210> SEQ ID NO 4
<211> LENGTH: 720
<212> TYPE: DNA
<213> ORGANISM: Aequorea victoria

<400> SEQUENCE: 4
atggctagca aaggagaaga actcttcact ggagttgtcc caattcttgt tgaattagat      60
ggtgatgtta acggccacaa gttctctgtc agtggagagg gtgaaggtga tgcaacatac     120
ggaaaactta ccctgaagtt catctgcact actggcaaac tgcctgttcc atggccaaca     180
ctagtcacta ctctgtgcta tggtgttcaa tgcttttcaa gatacccgga tcatatgaaa     240
cggcatgact ttttcaagag tgccatgccc gaaggttatg tacaggaaag gaccatcttc     300
ttcaaagatg acggcaacta caagacacgt gctgaagtca agtttgaagg tgataccctt     360
gttaatagaa tcgagttaaa aggtattgac ttcaaggaag atggcaacat tctgggacac     420
aaattggaat acaactataa ctcacacaat gtatacatca tggcagacaa acaaaagaat     480
ggaatcaaag tgaacttcaa gacccgccac aacattgaag atggaagcgt tcaactagca     540
gaccattatc aacaaaatac tccaattggc gatggccctg tccttttacc agacaaccat     600
tacctgtcca cacaatctgc cctttcgaaa gatcccaacg aaaagagaga ccacatggtc     660
cttcttgagt ttgtaacagc tgctgggatt acacatggca tggatgaact gtacaactga     720

<210> SEQ ID NO 5
<211> LENGTH: 1466
<212> TYPE: DNA
<213> ORGANISM: Saccharomyces cerevisiae

<400> SEQUENCE: 5
acgccccttc cttttcccct ttccttggtg tttgctatta ataaataatg tgcggagctc      60
aatcgtcata cgttcacgcc aggctccgga atcagagtac caatgcatgg gtacttattc     120
tcaaaatgct cttgccactc atccagtgcg tcaatctgtt cttttgtcag atcatctaag     180
ggatcgatag gctgatccca atctttaata acgtccagat cgaaggagtt caatgcaaga     240
ccacgcgacg catcatggcc tgcaaagtta gtgtatggcc cgcttggacc gtaaaactgc     300
ctccctcttg tgcagtcgta tactttgccc ctaatagcaa taaatatttt ttcatcgtcg     360
tggccgttaa atttggaaag cgtcctagga agaaattac ccgctactac cggttcacta     420
cctttattag aatcgtttgt gtttgaggcc ccgttacctg tgagcccggt tggatcctca     480
cttgttttaa cacctccaaa taacaagttt ttaatgaagg acatttgttc tctataatat     540
tccgatgtac gtgtgtgtgg ctgatgagat ttagactggt tagactattt gacgcgtcta     600
ttatagctta ctgcaacaag aaaatgatcg ttgatatata aactctcaga tgtatatatc     660
```

```
gttctggaaa catcgagcat aatacaatac aattcaacaa aaatgcgaga aggcactgat    720
gtcttgtcgt taaagaacca aaaacgcgga cactacgacc gtcttatttc cggtagaaaa    780
agggtacata cagttgaagg aacgaagaaa attaaaatta gaaaaaaaag taaaataaaa    840
caaggaaggt agggtaatat ggtctcgttt cctttgtcgc tccgcaaata aaggagctta    900
ttcccgcacg ctcacatggt aatttgcgcc aaatcacgga tgtggaaaac tgatcacgtg    960
cttcgatcgc caactactga gcgtcgtccc acactgatct ggcacagctt acctcgcctt   1020
gaaaatttta atctgtcctg ctcgtttgtt gtatattgct tcttctcaga atatgcccgc   1080
gataactgac aaagagggtt cgacgtttca gagattctac tcttgaccac tgtttcgtgt   1140
agccgctcaa ggtttatttc tttcttcttt aatgttcttg gcacttaggc ggctccgtcc   1200
tccgtctgaa attgccgatc ctattatttg cggagggctc cttagaaggg ctccttagta   1260
agcagtttgc gttcctgata taactccgtt cagaacaagg ataaagtcgc aataaccatt   1320
actaagcaca gtgttgtaag taggacaact cgaacctata taagggttgt gaactgtgct   1380
tgattcttgc ccatcatatg caaaaaagta cgtacttgat atatacaaca actgtagttc   1440
agtatagcga agtttaaatt tagaag                                        1466

<210> SEQ ID NO 6
<211> LENGTH: 23
<212> TYPE: DNA
<213> ORGANISM: Artificial Sequence
<220> FEATURE:
<223> OTHER INFORMATION: Synthesized

<400> SEQUENCE: 6
acgccccttc cttttteect ttc                                             23

<210> SEQ ID NO 7
<211> LENGTH: 22
<212> TYPE: DNA
<213> ORGANISM: Artificial Sequence
<220> FEATURE:
<223> OTHER INFORMATION: Synthesized

<400> SEQUENCE: 7
cttctaaatt taaacttcgc ta                                              22
```